(12) United States Patent
Keener

(10) Patent No.: US 7,252,993 B2
(45) Date of Patent: Aug. 7, 2007

(54) PLASMIDS ENCODING THERAPEUTIC AGENTS

(75) Inventor: William K. Keener, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 442 days.

(21) Appl. No.: 10/800,052

(22) Filed: Mar. 12, 2004

(65) Prior Publication Data

US 2005/0202561 A1  Sep. 15, 2005

(51) Int. Cl.
*C12N 5/10* (2006.01)
*C12N 15/00* (2006.01)
*C07H 21/04* (2006.01)
*C12P 21/02* (2006.01)

(52) U.S. Cl. .................. 435/325; 435/320.1; 435/69.1; 536/23.4; 536/24.1

(58) Field of Classification Search ...................... None
See application file for complete search history.

(56) References Cited

U.S. PATENT DOCUMENTS 6,441,272 B1  8/2002  Ye

FOREIGN PATENT DOCUMENTS

WO  WO 01/60393  *  8/2001

OTHER PUBLICATIONS

"Trends in lignin modification: a comprehensive analysis of the effects of genetic manipulations/mutations on lignification and vascular integrity" Anterola, Aldwin M. and Lewis, Norman G., Photochemistry 61 (2002) 221-294.

* cited by examiner

*Primary Examiner*—Daniel M. Sullivan
(74) *Attorney, Agent, or Firm*—Clayton, Howarth & Cannon

(57) ABSTRACT

Plasmids encoding anti-HIV and anti-anthrax therapeutic agents are disclosed. Plasmid pWKK-500 encodes a fusion protein containing DP178 as a targeting moiety, the ricin A chain, an HIV protease cleavable linker, and a truncated ricin B chain. N-terminal extensions of the fusion protein include the maltose binding protein and a Factor Xa protease site. C-terminal extensions include a hydrophobic linker, an L domain motif peptide, a KDEL ER retention signal, another Factor Xa protease site, an out-of-frame buforin II coding sequence, the lacZα peptide, and a polyhistidine tag. More than twenty derivatives of plasmid pWKK-500 are described. Plasmids pWKK-700 and pWKK-800 are similar to pWKK-500 wherein the DP178-encoding sequence is substituted by RANTES- and SDF-1-encoding sequences, respectively. Plasmid pWKK-900 is similar to pWKK-500 wherein the HIV protease cleavable linker is substituted by a lethal factor (LF) peptide-cleavable linker.

4 Claims, No Drawings

PLASMIDS ENCODING THERAPEUTIC AGENTS

CONTRACTUAL ORIGIN OF THE INVENTION

The United States Government has rights in the following invention pursuant to Contract No. DE-AC07-99ID13727 between the U.S. Department of Energy and Bechtel BWXT Idaho, LLC.

BACKGROUND OF THE INVENTION

This invention relates to antiviral agents, antimicrobial agents, and methods of use thereof. More particularly, illustrative embodiments of the invention relate to plasmids that encode antiviral agents that specifically destroy cells infected by human immunodeficiency viruses ("HIV") that produce a protease in such infected cells. These antiviral agents are activated by the HIV protease, thereby specifically targeting HIV-infected cells for destruction. Other illustrative embodiments of the invention relate to plasmids that encode antimicrobial agents that specifically destroy cells infected by selected pathogenic microbes, such as *Bacillus anthracis*, the causal agent of anthrax.

Toxins that target cell surface receptors or antigens on tumor cells have attracted considerable attention for treatment of cancer. E.g., I. Pastan & D. FitzGerald, Recombinant Toxins for Cancer Treatment, 254 Science 1173-1177 (1991); Anderson et al., U.S. Pat. Nos. 5,169,933 and 5,135,736; Thorpe et al., U.S. Pat. No. 5,165,923; Jansen et al., U.S. Pat. No. 4,906,469; Frankel, U.S. Pat. No. 4,962,188; Uhr et al., U.S. Pat. No. 4,792,447; Masuho et al., U.S. Pat. Nos. 4,450,154 and 4,350,626. These agents include a cell-targeting moiety, such as an antigen-binding protein or a growth factor, linked to a plant or bacterial toxin. They kill cells by mechanisms different from conventional chemotherapy, thus potentially reducing or eliminating cross resistance to conventional chemotherapeutic agents.

Ricin and other similar plant toxins, such as abrin, modeccin and viscumin, comprise two polypeptide chains (known as the A and B chains) linked by a disulfide bridge, one chain (the A chain) being primarily responsible for the cytotoxicity and the other chain (the B chain) having sites that enable the molecule to bind to cell surfaces. Such toxins are known as type II ribosome-inactivating proteins or RIPs. F. Stirpe et al., Ribosome-inactivating Proteins from Plants: Present Status and Future Prospects, 10 Biotechnology 405-412 (1992).

Ricin is produced in the plant *Ricinus communis* (commonly known as the castor bean plant) via a precursor protein known as "preproricin." Preproricin comprises a single polypeptide chain that includes a leader sequence, the A chain, a linker peptide, and the B chain. The leader sequence is subsequently removed in the organism to yield proricin, which is then cleaved to eliminate the linker region such that the A and B chains remain connected only by a disulfide bond in the mature protein. The toxicity of ricin-type toxins operates in three phases: (1) binding to the cell surface via the B chain; (2) penetration of at least the A chain into the cytosol via intracellular organelles, and (3) inhibition of protein synthesis through the A chain cleaving an essential adenine residue from ribosomal RNA. Thus, outside the cell separated A and B chains are essentially non-toxic, because the inherently toxic A chain lacks the ability to bind to cell surfaces and enter the cells in the absence of the B chain. Moreover, preproricin and proricin are also non-toxic, since the activity of the A chain is inhibited in these precursors.

It is also known that in ricin-type toxins the B chain binds to cell surfaces by virtue of galactose recognition sites, which react with glycoproteins or glycolipids exposed on the cell surface. It has been suggested that the toxicity of the ricin A chain might be exploited in anti-tumor therapy by replacing the indiscriminately-binding B chain with a different targeting component having the ability to bind only to tumor cells. Thus, various immunotoxins have been prepared consisting of a conjugate of whole ricin or a separated ricin A chain and a tumor-specific monoclonal antibody or other targeting component.

While previously described immunotoxins comprising ricin are generally suitable for their specific purposes, they possess certain inherent limitations that detract from their overall utility in treating viral or microbial infections. One problem with the known conjugates arises from a structural feature of the A chain from natural ricin. It is known that the natural ricin A chain becomes N-glycosylated during its synthesis, by enzymes present in *Ricinus* cells, and it is thought that the resulting sugar moieties are capable of non-specific interactions with cell surfaces. Thus, it appears that the known A chain conjugates are capable of a certain amount of binding with non target cells, even in the absence of the natural B chain, thus increasing the toxicity of such immunotoxins toward non-target cells. To partially mitigate this problem, recombinant A chain that lacks carbohydrate residues has been produced in *E. coli*. S. H. Pincus & V. V. Tolstikov, Anti-Human Immunodeficiency Virus Immunoconjugates, 32 Adv. Pharmacol. 205-247 (1995). Another problem with many ricin immunoconjugates arises from the fact that the B chain seems to have an important secondary function in that it somehow assists in the intoxication process, apart from its primary function in binding the ricin molecule to the cell surfaces. This secondary function is lost if the B chain is replaced by a different targeting component, such as a monoclonal antibody. Some researchers have addressed this problem by covalent attachment of affinity reagents to the B chain such that the galactose binding sites are blocked. J. M. Lambert et al., An Immunotoxin Prepared with Blocked Ricin: a Natural Plant Toxin Adapted for Therapeutic Use, 51 Cancer Res. 6236-6242 (1991).

The aforementioned modifications of ricin seek to enhance binding specificity to the outer cell surface by immunotoxins and similar, targeted therapeutic agents. Since certain types of infected cells do not express infection-related surface antigens, such binding specificity represents an inherent limitation. S. H. Pincus & V. V. Tolstikov, supra. A targeting-independent agent with a well-defined toxin activation mechanism involving a viral protease would permit the use of nonspecific "targeting" (i.e., cell-binding) molecules, including sugar moieties and fully active ricin B chain. Therapeutic agents designed in this manner could eliminate a broader spectrum of infected cells, with potentially fewer undesirable side effects.

Anti-HIV immunotoxins have been described that include antibodies linked to various toxic moieties via a peptide linker that includes a sequence cleavable by HIV protease. S. H. Pincus & V. V. Tolstikov, supra. In some cases, release of the toxic moiety by this protease may render it active, although the specific activation mechanism was not further defined.

U.S. Pat. No. 6,627,197 to W. K. Keener et al. describes antiviral toxins wherein an HIV protease cleavage site is interposed between ricin A and B chains. In ricin, the natural site for cleavage by proteolytic activity in *Ricinus* is in a disulfide-circumscribed loop in which one cysteine resides on the A chain and the other resides on the B chain; cleavage yields A and B chains connected by a disulfide bond. Therefore, U.S. Pat. No. 6,627,197 describes an HIV-protease cleavage sequence fused in-frame to the C-terminus of A chain such that the natural cleavage site is replaced with the HIV-protease site in the disulfide-circumscribed loop. In these embodiments, at lease some minimal N-terminal sequence of B chain required to inhibit A chain activity is retained, such that activation requires proteolytic cleavage and reduction of the disulfide bond.

As exemplified by U.S. Pat. No. 6,627,197, fusion proteins containing toxins have started to replace immunotoxins, which require chemical linking of the toxin to antibodies that bind cells. Such fusion proteins may contain portions of antibodies as targeting moieties. With an active toxin, the choice of targeting moieties is limited. Signal sequences, which are much shorter than antibodies, may promote translocation of agents into cells and increase the potency of the agents. Further, activatable toxins broaden the choices of targeting moieties. Further, conventional plasmid preparation is time consuming, thus restricting the number that can be tested. The development of highly versatile plasmids would accelerate the testing of signal sequences.

In view of the foregoing, it will be appreciated that providing highly versatile plasmids that permit the easy testing of signal sequences together with activatable toxins would be a significant advancement in the art.

BRIEF SUMMARY OF THE INVENTION

It is a feature of the present invention to provide plasmids encoding activatable toxins. These plasmids are highly versatile and permit the easy construction of numerous derivatives.

These and other features are present in plasmids pWKK-500, pWKK-700, pWKK-800, pWKK-900, pWKK-21, and their derivatives.

Another illustrative embodiment of the invention comprises a plasmid encoding an anti-HIV therapeutic agent comprising a fusion protein comprising a DP178 peptide as a targeting moiety and a ricin A chain as a polypeptide toxin, wherein the plasmid is a member selected from the group consisting of pWKK-500, pWKK-501, pWKK-502, pWKK-503, pWKK-504, pWKK-505, pWKK-506, pWKK-507, pWKK-508, pWKK-509, pWKK-510, pWKK-511, pWKK-512, pWKK-513, pWKK-514, pWKK-515, pWKK-516, pWKK-517, pWKK-518, pWKK-519, and pWKK-520. The fusion proteins of many of these plasmids also include an HIV protease cleavable linker and a truncated portion of a ricin B chain.

Still another illustrative embodiment of the present invention comprises a plasmid encoding an anti-HIV therapeutic agent comprising a fusion protein comprising a RANTES peptide as a targeting moiety and a ricin A chain as a polypeptide toxin, wherein the plasmid is a member selected from the group consisting of pWKK-700, pWKK-701, pWKK-702, pWKK-703, pWKK-704, pWKK-705, pWKK-706, pWKK-707, pWKK-708, pWKK-709, pWKK-710, pWKK-711, pWKK-712, pWKK-713, pWKK-714, pWKK-715, pWKK-716, pWKK-717, pWKK-718, pWKK-719, pWKK-720, pWKK-721, and pWKK-722. Similar to the fusion proteins encoded by the pWKK-500 series of plasmids, the fusion proteins of many of these plasmids also include an HIV protease cleavable linker and a truncated portion of a ricin B chain.

Yet another illustrative embodiment of the present invention comprises a plasmid encoding an anti-HIV therapeutic agent comprising a fusion protein comprising an SDF-1 peptide as a targeting moiety and a ricin A chain as a polypeptide toxin, wherein the plasmid is a member selected from the group consisting of pWKK-800, pWKK-801, pWKK-802, pWKK-803, pWKK-804, pWKK-805, pWKK-806, pWKK-807, pWKK-808, pWKK-809, pWKK-810, pWKK-811, pWKK-812, pWKK-813, pWKK-814, pWKK-815, pWKK-816, pWKK-817, pWKK-818, pWKK-819, pWKK-820, and pWKK-821. Similar to the fusion proteins encoded by the pWKK-500 series of plasmids, the fusion proteins of many of these plasmids also include an HIV protease cleavable linker and a truncated portion of a ricin B chain.

Still another illustrative embodiment of the invention comprises a plasmid encoding an anti-anthrax therapeutic agent comprising a fusion protein comprising a DP178 peptide as a targeting moiety and a ricin A chain as a polypeptide toxin, wherein the plasmid is a member selected from the group consisting of pWKK-900, pWKK-901, pWKK-902, pWKK-903, pWKK-904, pWKK-905, pWKK-906, pWKK-907, pWKK-908, pWKK-909, pWKK-910, pWKK-911, pWKK-912, pWKK-913, pWKK-914, pWKK-915, pWKK-916, pWKK-917, pWKK-918, pWKK-919, and pWKK-920. The fusion proteins of many of these plasmids also include a Lethal Factor protease cleavable linker and a truncated portion of a ricin B chain.

Another illustrative embodiment of the invention comprises a plasmid encoding an anti-HIV therapeutic agent comprising a fusion protein comprising a one-domain ricin B chain as a targeting moiety and a ricin A chain as a polypeptide toxin, wherein the plasmid is a member selected from the group consisting of pWKK-21, pWKK-21a, pWKK-21b, pWKK-21c, and pWKK-21d.

Additional illustrative embodiments of the invention comprise derivatives of plasmid pWKK-500 wherein two or more of the derivation procedures for making derivative plasmids pWKK-501 through pWKK-520 are performed to pWKK-500, where such derivation procedures are not mutually exclusive. Similarly, "multiple derivatives" of plasmids pWKK-700, pWKK-800, pWKK-900, and pWKK-21 are also illustrative embodiments of the present invention.

Still another illustrative embodiment of the invention comprises an oligonucleotide cassette represented by SEQ ID NO:36, which encodes an HIV protease-cleavable peptide linker. Yet another illustrative embodiment of the invention comprises an oligonucleotide cassette encoding an alternative HIV-protease-cleavable peptide linker. This cassette can be made by annealing oligonucleotides represented by SEQ ID NO:18 and SEQ ID NO:19.

A further illustrative embodiment of the invention comprises a method for making a modified plasmid encoding a modified fusion protein, the method comprising:

(a) providing a base plasmid selected from the group consisting of pWKK-500 and derivatives thereof, pWKK-700 and derivatives thereof, pWKK-800 and derivatives thereof, pWKK-900 and derivatives thereof, and pWKK-21 and derivatives thereof, the base plasmid comprising a plurality of DNA segments that encode a base fusion protein, wherein the base fusion protein comprises functional elements comprising a targeting moiety, a polypeptide toxin, and optionally one or more peptides selected from the group consisting of maltose binding protein, Factor Xa site, myristylation signal, flexible linker, protease-cleavable linker, L domain motif, KDEL ER retention signal, hydrophilic linker comprising out-of-frame buforin II, lacZa peptide, and polyhistidine tag, wherein each of the plurality of DNA segments is flanked by unique restriction endonuclease sites, and digesting the base plasmid with restriction endonucleases corresponding to selected unique restriction endonuclease sites such that one of the plurality of DNA segments is removed from the base plasmid; and (b) ligating a replacement DNA segment to the base plasmid from which one of the plurality of DNA segments is removed, wherein the replacement DNA segment encodes a replacement functional element that replaces one of the functional elements of the base fusion protein, thereby resulting in a modified plasmid encoding a modified fusion protein.

DETAILED DESCRIPTION

Before the present plasmids encoding anti-HIV therapeutic agents and anti-microbial therapeutic agents are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms “a,” “an,” and “the” include plural referents unless the context clearly dictates otherwise. Thus, for example, reference to a fusion protein comprising “a functional element” includes reference to a fusion protein comprising two or more of such functional elements, reference to a plasmid encoding “an activatable toxin” includes reference to a plasmid encoding two or more of such activatable toxins, and reference to a pharmaceutical composition comprising “the pharmaceutically acceptable carrier” includes reference to a pharmaceutical composition comprising two or more of such pharmaceutically acceptable carriers.

In describing and claiming the present invention, the following terminology will be used in accordance with the definitions set out below.

As used herein, “comprising,” “including,” “containing,” “characterized by,” and grammatical equivalents thereof are inclusive or open-ended terms that do not exclude additional, unrecited elements or method steps. “comprising” is to be interpreted as including the more restrictive terms “consisting of” and “consisting essentially of.”

As used herein, “consisting of” and grammatical equivalents thereof exclude any element, step, or ingredient not specified in the claim.

As used herein, “consisting essentially of” and grammatical equivalents thereof limit the scope of a claim to the specified materials or steps and those that do not materially affect the basic and novel characteristic or characteristics of the claimed invention.

As used herein, “PCR” means polymerase chain reaction, as is well known in the art. PCR is illustratively described in U.S. Pat. Nos. 4,683,195; 4,683,202; 4,800,159; 4,965,188; PCR Technology: Principles and Applications for DNA Amplification (H. Erlich ed., Stockton Press, New York, 1989); and PCR Protocols: A guide to Methods and Applications (Innis et al. eds, Academic Press, San Diego, Calif., 1990).

As used herein, “MBP” means maltose binding protein.

As used herein, “bp” means base pairs.

As used herein, “stretch” means a sequence of amino acid residues.

As used herein, “derivatives” of pWKK-500 means plasmids constructed from pWKK-500, such as according to Examples 2-21, 38, and 39. Similarly, derivatives of pWKK-700 are plasmids constructed from pWKK-700, such as according to Examples 23-25, 40, and 41. Similarly, derivatives of pWKK-800 are plasmids constructed from pWKK-800, such as according to Examples 27, 28, 42, and 43. Similarly, derivatives of pWKK-21 are plasmids constructed from pWKK-21, such as according to Example 44.

As used herein, a “pharmaceutically acceptable” component is one that is suitable for use with humans and/or animals without undue adverse side effects (such as toxicity, irritation, and allergic response) commensurate with a reasonable benefit/risk ratio. The term “carrier” refers to a diluent, adjuvant, excipient, or vehicle with which the activatable toxin is administered. Such pharmaceutical carriers can be sterile liquids, such as water, saline, dextrose, glycerol, ethanol, and the like; and if desired, minor amounts of auxiliary substances such as wetting or emulsifying agents, buffers, and the like can be added.

As used herein, “administering” and similar terms mean delivering the composition to the individual being treated such that the composition is capable of being circulated systemically to the parts of the body where the targeting portion of the activatable toxin can bind its target. Thus, the activatable toxin is illustratively administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion.

As used herein, “peptide” means peptides of any length and includes proteins. The terms “polypeptide” and “oligopeptide” are used herein without any particular intended size limitation, unless a particular size is otherwise stated.

Activatable toxins, such as HIV-protease-activated toxins, provide a selection mechanism that enables the use of targeting moieties that bind to healthy, but HIV-susceptible cells. These targeting moieties are much smaller than antibodies and are more suitable for use in fusion proteins than are antibodies. Targeting moieties used in the present invention include DP178 (also known as T-20), a known ligand/agonist of the phagocyte N-formyl peptide receptor (FPR) and of the similar FPR-like 1 receptor (FPRL1R), which occur on monocytes and macrophages derived therefrom. DP178 is a targeting moiety used in the pWKK-500 series of plasmids described herein. RANTES (regulated on activation, normal T-cell expressed and secreted) is a natural ligand to CCR5, which is a chemokine co-receptor for HIV entry into cells. RANTES is a targeting moiety used in the pWKK-700 series of plasmids described herein. SDF-1 (stromal cell-derived factor-1) is a natural ligand to CXCR4, which is a chemokine co-receptor for HIV entry into cells. SDF-1 is a targeting moiety used in the pWKK-800 series of plasmids described herein.

The plasmids of the present invention are very versatile due to carefully constructed DNA sequences that permit a variety of simple manipulations, such as excising selected DNA segments followed by recircularization, to provide multiple derivative plasmids with various structures of the encoded proteins. These plasmids have been constructed using DNA cassettes, which can be easily inserted or removed and, thus, provide even greater versatility. For example, DNA cassettes encoding the DP178, RANTES, and SDF-1 targeting peptides are flanked by unique restriction endonuclease sites, which permit insertion and/or excision of such cassettes using restriction endonucleases and other standard techniques used in recombinant DNA technology. Cassettes encoding markers, such as the alpha peptide of β-galactosidase, have been inserted into many of these plasmids to permit color detection of expressed proteins by alpha complementation. Still further, cassettes encoding affinity tags have been inserted into many of these plasmids to facilitate the obtaining of highly pure preparations of the fusion protein. For example, the maltose binding protein (MBP) has an affinity for amylose, and fusion proteins comprising MBP can be purified by affinity chromatography. O. K. Kellerman & T. Ferenci, Maltose-binding protein from *Escherichia coli*, 90 Meth. Enzymol. 459-463 (1982). Further, a polyhistidine peptide (e.g., $(His)_6$) has affinity for nickel, and fusion proteins comprising $(His)_6$ can also be purified by nickel affinity chromatography. U.S. Pat. No. 5,395,753. Moreover, a cassette encoding a protease-cleavable linker has been inserted into these plasmids. For example, a cassette encoding an HIV protease-cleavable linker has been inserted into many of these plasmids. Still further, a cassette encoding a cell-toxic protein (e.g., ricin A chain) has been inserted into these plasmids. It should be appreciated that these cassettes can be removed or substituted with other cassettes according to methods well known in the art of recombinant DNA. For example, cassettes encoding cell-targeting peptides, cleavable linkers, cell-toxic proteins, and the like can be removed or substituted with other appropriate cassettes encoding other functional peptides or proteins, now known or yet to be discovered. These derivatives can be made according to techniques well known in the art.

The pWKK-500 series of plasmids is based on plasmid pWKK-500, which can be quickly converted to at least twenty other plasmids with varying C- and N-terminal coding sequences without adding DNA. That is, the potential variations are encoded within the reading frames of plasmid pWKK-500 itself. The versatility of pWKK-500 is made possible by strategically located unique restriction sites. In many cases, the derivative plasmid formed from pWKK-500 will have new restriction sites across the ligation junction or will have existing sites preserved across the junction. Thus, screening of candidate plasmids is facilitated according to methods well known in the art of recombinant DNA technology.

Many such derivatives have C-terminal "amber-ED tracers," which facilitate tracking during protein purification. An amber-ED tracer comprises a C-terminal extension beyond an amber stop codon that includes the enzyme donor (ED) fragment of β-galactosidase. The tracer extensions occur in a fraction of the fusion protein molecules synthesized in amber suppressing *E. coli* strains, such as XL1 Blue (Stratagene, Catalog No. 200228, La Jolla, Calif.), which insert glutamine residues at amber codons (supE44 genotype). To prevent the extensions, the plasmid is simply transferred to a non-suppressing host. Other plasmid derivatives have C-terminal versions of buforin II, which may act as a targeting moiety for incorporation into HIV particles. Still other derivatives encode no HIV-protease-cleavable linker. These plasmids have amber-ED tracers after the ricin A chain and can be used to create targeted ricin A chain variations as therapeutic agents.

All genetic elements within pWKK-500 that encode functional moieties or functional elements are flanked by unique restriction sites. In particular, the elements encoding the DP178 targeting peptide and the HIV-protease-cleavable linker are flanked by multiple unique restriction sites.

Upstream of the DP178 targeting moiety in the pWKK-500 series of plasmids, of the RANTES targeting moiety in the pWKK-700 series of plasmids, and of the SDF-1 targeting moiety in the pWKK-800 series of plasmids are coding sequences for the maltose binding protein (MBP) and a Factor Xa recognition site. After expression of the fusion protein in bacteria, according to methods well known in the art, the fusion protein can be purified by affinity chromatography using amylose as a ligand to bind the MBP-containing fusion protein. Digestion of the fusion protein with Factor Xa protease cleaves the fusion protein between the MBP portion and the targeting moiety, thus removing the MBP from the remainder of the therapeutic agent.

Many of the plasmids also encode a polyhistidine peptide downstream of an amber stop codon. In fusion proteins comprising polyhistidine, the fusion protein can be purified using nickel affinity chromatography, as mentioned above. Since another Factor Xa site occurs between the polyhistidine and the glutamine residue encoded by the amber codon in suppressor strains, the polyhistidine can be removed from the fusion protein by digestion with Factor Xa protease, and the polyhistidine can be separated from the remainder of the fusion protein by affinity to nickel resins.

The plasmids of the present invention can be used for making fusion proteins in gene expression systems, which are well known in the art. These fusion proteins can be tested as therapeutic agents for treating HIV and other microbial infections, such as anthrax. The plasmids can also be used as platforms for making derivatives, wherein other DNA segments encoding targeting moieties, cleavable linkers, and cell-toxic proteins, can easily be substituted for the current functional elements. Further, the DNA encoding the fusion proteins can be used as therapeutic agents, provided that appropriate promoters and other signals are provided.

The fusion proteins encoded by the plasmids of the present invention can be isolated by, first culturing *E. coli* cells containing the plasmids in an appropriate bacterial growth medium, typically at 37° C. Expression of the fusion protein is induced by adding an inducer of the tac promoter, such as isopropylthiogalactoside (IPTG). After incubation, the cells are harvested and lysed. The fusion protein is then purified. In cases where the maltose binding protein or a polyhistidine tag comprise the fusion protein, purification is most easily carried out by affinity chromatography according to methods well known in the art. The affinity tags can be removed, such as by digestion with Factor Xa protease, and the resulting fusion protein minus the affinity tags is concentrated. This concentrated fusion protein is then tested for efficacy as an activatable toxin.

The activatable toxin is typically formulated for administration to an individual in need of such treatment by mixing with a pharmaceutically acceptable carrier. The resulting composition is administered such that the activatable toxin circulates in the body for access to target cells. After the activatable toxin is taken up by target cells, the protease-cleavable peptide linker is digested by protease in the cell, such as HIV protease. Digestion of the protease-cleavable linker activates the polypeptide toxin (e.g., ricin A chain), which results in killing of the target cell.

EXAMPLE 1 pWKK-500

The plasmid pWKK-500 contains the coding sequences for several functional elements cloned into the pMAL-p2X plasmid (New England Biolabs, Beverly, Mass.; SEQ ID NO:1), which encodes the lacZa, or enzyme donor (ED), fragment of β-galactosidase. These coding sequences for the functional elements are arranged in the following order: maltose binding protein (MBP), Factor Xa site, myristylation signal, DP178, flexible linker, ricin A chain, HIV protease cleavable linker, ricin B chain (truncated), repeat of hydrophobic C-terminal stretch of ricin A chain, L domain motif, KDEL ER retention signal, amber (TAG) stop codon, Factor Xa site, hydrophilic linker (out-of-frame buforin II; SEQ ID NO:43), lacZα peptide (ED), (His)$_6$ tag, TGA stop codon. The nucleotide sequence of this sequence of functional elements is set forth as SEQ ID NO:2.

Plasmid pMAL-p2X is an *E. coli* plasmid cloning vector designed for recombinant protein expression and purification using a maltose binding protein fusion and purification system (New England Biolabs, cat. no. NEB #E8000S). C. Di Guan et al., Vectors that facilitate the expression and purification of foreign peptides in *Escherichia coli* by fusion to maltose-binding protein, 67 Gene 21-30 (1988); C. V. Maina et al., An *Escherichia coli* vector to express and purify foreign proteins by fusion to and separation from maltose-binding protein, 74 Gene 365-373 (1988); P. Riggs, in Current Protocols in Molecular Biol. (F. M. Ausubel et al., eds, Greene Associates/Wiley Interscience, New York 1992). It contains the pMB1 origin of replication from pBR322 and is maintained at a copy number similar to that of pBR322. In addition, pMAL-p2X also contains an M13 origin of replication. R. J. Zagursky & M. L. Berman, Cloning vectors that yield high levels of single-stranded DNA for rapid DNA sequencing, 27 Gene 183-191 (1984).

The multiple cloning site (MCS) is positioned to allow translational fusion of the *E. coli* maltose binding protein (MBP, encoded by the malE gene) to the N-terminus of the cloned target protein. MBP=s affinity for amylose allows easy purification of the fusion protein, and the MBP domain can be removed later using Factor Xa protease. P. Riggs, in Current Protocols in Molecular Biol. (F. M. Ausubel et al., eds, Greene Associates/Wiley Interscience, New York 1992). Cloning of the target gene at the MCS disrupts expression of lacZα, allowing for insert screening by α-complementation.

Transcription of the gene fusion is controlled by the inducible "tac" promoter ($P_{tac}$). Basal expression from $P_{tac}$ is minimized by the binding of the Lac repressor, encoded by the lacI$^q$ gene, to the lac operator immediately downstream of $P_{tac}$. A portion of the rrnB operon containing two terminators, derived from the vector pKK233-2, prevents transcription originating from $P_{tac}$ from interfering with plasmid functions.

The coding sequences for the various functional elements of pMAL-p2X are located at the nucleotide coordinates indicated in parentheses following each feature: lacI$^q$ (81-1163), $P^{tac}$ (1406-1433), malE (1528-2703), MCS (2703-2809), lacZα (2810-2991), bla (ampicillin resistance, 3493-4353), M13 origin (4395-4908), pMB1 origin (5019-5607), rop (6228-6037).

In pWKK-500 (SEQ ID NO:2), the MBP is coded for at nucleotides 7-1182. The Factor Xa site is an Ile-Glu-Gly-Arg (SEQ ID NO:3) recognition sequence for Factor Xa protease. The Factor Xa site is encoded at nucleotides 1207-1218 of SEQ ID NO:2 (pWKK-500). The myristylation signal comprises a Gly-Ala-Arg-Ala-Ser peptide (SEQ ID NO:4) for in vivo attachment of myristic acid to the N-terminal G residue exposed by Factor Xa. The coding sequence for the myristylation signal is located at nucleotides 1219-1233 of SEQ ID NO:2 (pWKK-500). DP178 (SEQ ID NO:5) is an ectodomain peptide of HIV gp41, which binds to gp41 on HIV particles. The coding sequence for DP178 is located at nucleotides 1234-1341 of SEQ ID NO:2 (pWKK-500). The flexible linker (SEQ ID NO:6) is a peptide linker based on the antibody hinge region. The flexible linker is encoded at nucleotides 1342-1389 of SEQ ID NO:2 (pWKK-500). The ricin A chain (SEQ ID NO:7) is encoded at nucleotides 1390-2190 of SEQ ID NO:2 (pWKK-500). The HIV protease cleavable linker is a peptide sequence (Val-Ser-Gin-Asn-Tyr-Pro-Ile-Val-Gln-Asn, SEQ ID NO:8) wherein cleavage by HIV protease occurs between the Tyr and Pro residues. This cleavage reaction activates the ricin A chain. This HIV protease cleavable linker is coded for at nucleotides 2191-2220 of SEQ ID NO:2 (pWKK-500). The coding sequence for a truncated version of the ricin B chain is found at nucleotides 2224-2265 of SEQ ID NO:2 (pWKK-500). This truncated ricin B chain includes only the N-terminal sequence followed by a Pro residue (Ala-Asp-Val-Cys-Met-Asp-Pro-Glu-Pro-Leu-Val-Arg-Ile-Pro, SEQ ID NO:9). A variant of the repeat of a hydrophobic stretch near the C terminus of ricin A chain (Val-Ser-Ile-Leu-Ile-Pro-Ile-Ile-Ala-Leu-Ala-Ser-Ala, SEQ ID NO:10) is encoded at nucleotides 2266-2304 of SEQ ID NO:2 (pWKK-500). The natural sequence (Val-Ser-Ile-Leu-Ile-Pro-Ile-Ile-Ala-Leu-Met-Val; SEQ ID NO:38) is putatively involved in facilitating translocation of ricin A chain across membranes. J. C. Simpson et al., Point mutations in the hydrophobic C-terminal region of ricin A chain indicate that Pro 250 plays a key role in membrane translocation, 232 Eur. J. Biochem. 458-463 (1995). The L domain motif (Pro-Pro-Pro-Pro-Tyr, SEQ ID NO:11) from Rous sarcoma virus interacts with ubiquitin protein ligases, such as Nedd4, which can result in covalent attachment of ubiquitin to lysine residues, perhaps the lysine of the KDEL signal following the L domain motif. While polyubiquitination of ricin A chain variants with multiple additional lysines increases proteasomal degradation, monoubiquitination of proteins can lead to other pathways and could permit the antiviral agent to interact with Tsg101, a protein that interacts with HIV-1 Gag as it traverses the endocytic trafficking pathway to the plasma membrane, where virions are released. Since Tsg101 binds to ubiquitinated proteins as well as Gag, the L domain motif may cause the antiviral agent to be incorporated into maturing virus particles, where its activation by HIV-1 protease is more probable. The L domain motif is encoded at nucleotides 2305-2319 of SEQ ID NO:2 (pWKK-500). The KDEL ER retention signal (Lys-Asp-Glu-Leu, SEQ ID NO:12) is known to enhance toxicity of the ricin A chain. It is coded for at nucleotides 2323-2334 of SEQ ID NO:2 (pWKK-500). An amber (TAG) stop codon is located at nucleotides 2335-2337. Following the amber stop codon and in the same reading frame there is another Factor Xa site (Ile-Glu-Gly-Arg, SEQ ID NO:3). This Factor Xa site is encoded at nucleotides 2356-2367 of SEQ ID NO:2 (pWKK-500). C. A. Carter, Tsg101: HIV-1's Ticket to Ride, 10 Trends Microbiol. 203-205 (2002); A. Kikonyogo et al., Proteins related to the Nedd4 family of ubiquitin protein ligases interact with the L domain of Rous sarcoma virus and are required for gag budding from cells, 98 Proc. Nat=1 Acad. Sci. USA 11199-11204 (2001); E. D. Deeks, The low lysine content of ricin A chain reduces the risk of proteolytic degradation after translocation from the endoplasmic reticulum to the cytosol, 41 Biochemistry 3405-3413 (2002); J. Zhan et al., Modification of ricin A chain, by addition of endoplasmic reticulum (KDEL) or Golgi (YQRL) retention sequences, enhances its cytotoxicity and translocation, 46 Cancer Immunol. Immunother. 55-60 (1998).

At nucleotides 2351-2413 there is a buforin II peptide (SEQ ID NO:14) coded out-of-frame to the MBP-containing fusion peptide. When read in the same reading frame as the immediately preceding Factor Xa site, this buforin II coding segment codes for a hydrophilic linker (SEQ ID NO:43). Buforin II is an antimicrobial peptide of 21 amino acid residues derived from a histone protein and found in the gut of the Asian toad. It has activity against many bacteria, including *E. coli*. It binds to negatively charged bacterial membranes and crosses them without creating pores. It exerts antimicrobial activity by binding to RNA and DNA in the cell. It is much less toxic to mammalian cells, apparently because the cell surfaces are composed of zwitterionic phospholipids, which do not act as receptors for the positively charged buforin II as do bacterial phospholipids. An intriguing finding of structure/function studies is that the Pro residue of buforin II is important for traversing membranes. The amphipathic alpha helix after the Pro residue is apparently responsible for binding nucleic acids and for crossing membranes. S. Kobayashi et al., Interactions of the novel antimicrobial peptide buforin 2 with lipid bilayers: proline as a translocation promoting factor, 39 Biochemistry 8648-8654 (2000).

Expression of buforin II may have a toxic effect on the bacterial host and limit the amount of fusion protein product. Therefore, the amber-ED tracers will be important for rapidly verifying product formation. Fusion to the MBP-containing fusion protein probably lessens buforin antimicrobial activity, however, it may still permit crossing of membranes by the full length protein and binding to HIV RNA. This could have a targeting effect, leading to incorporation of the therapeutic protein into forming viral particles (i.e., packaged viral RNA) where it is more likely to be activated by HIV protease activity. Indeed, some antiviral agents may be activated after release of the virion from the plasma membrane, leading to the destruction of cells infected by such compromised virions and thereby precluding viral replications. Of note, the pMAL-p2X-derived proteins are exported to the periplasm, thus, antimicrobial activity upon expression would imply that the entire construct is able to traverse the bacterial membrane. J. Gatlin et al., Regulation of intracellular human immunodeficiency virus type-1 protease activity, 244 Virology 87-96 (1998).

The one-step creation of buforin II fusions without additional DNA is the best approach to determining if the product is too toxic for expression. The rearrangement of the plasmid can be expected to occur with very high efficiency, whereas insertion of new DNA typically occurs with less efficiency. If transformed *E. coli* cells do not grow after transformation with a rearranged plasmid having C-terminal buforin II, then it can be assumed that such constructs are too toxic.

Native buforin II includes a Gly-Arg dipeptide, which is likely to be a secondary site for Factor Xa protease digestion. To avoid unwanted digestion at this site, a Leu codon was inserted to convert the Gly-Arg dipeptide to a Gly-Leu-Arg tripeptide. To permit conversion back to the natural sequence, the nucleotide sequence was constructed such that treatment of the DNA with Bsu36I restriction endonuclease, then mung bean nuclease, followed by religation will eliminate the Leu codon. To verify the proper sequence, a unique EagI restriction endonuclease site is created upon religation.

The first four residues of native buforin II are not required for activity. The initial Thr residue was omitted in the construction of pWKK-500.

Following the buforin II coding region there is the coding region for the lacZα peptide or ED. This peptide is encoded at nucleotides 2425-2764 of pWKK-500. Following the ED peptide, there is encoded at nucleotides 2783-2800 a polyhistidine region. A TGA stop codon is at nucleotides 2801-2803.

Certain *E. coli* host strains have the supE44 genotype, which enables insertion of a Gln residue instead of stopping protein synthesis at TAG codons. Nucleotide residues adjacent to the TAG stop codon influence efficiency of suppression, i.e., Gln insertion. P. Edelman et al., Nonsense suppression context effects in *Escherichia coli* bacteriophage T4, 207 Mol. Gen. Genet. 517-518 (1987). A purine residue (A or G) immediately 3' to the TAG is preferred for amber suppression. It is expected that, in a suppressing host, Gln will be inserted with an efficiency of less than 100%. In the event of an insertion, translation will continue until a TAA or TGA stop codon is encountered. Note that a Factor Xa site is placed immediately following the TAG codon in pWKK-500, so that any extension of the fusion protein can be largely removed by Factor Xa cleavage. While the residual Factor Xa site remaining after its cleavage will undoubtedly destroy KDEL functionality, the fraction of protein molecules with nonfunctional KDEL sequences can be tolerated to realize certain advantages described below. The residues remaining after Factor Xa cleavage should not affect other functions.

By combining the fusion protein with the enzyme acceptor (EA) fragment of β-galactosidase, a sensitive enzyme assay is obtained that will facilitate tracking of protein during purification. During amylose resin affinity chromatography, protein molecules with extensions should be co-purified with molecules without extensions.

Digestion with Factor Xa can be monitored to ensure that overdigestion does not occur. A C-terminal peptide including ED that is liberated by Factor Xa cleavage can be easily separated by ultrafiltration, such as with a Microcon YM-100 ultrafiltration unit. When the amount of ED activity in the filtrate no longer increases, digestion can be stopped.

The first Factor Xa genetic element can be replaced with an enterokinase recognition sequence (Asp-Asp-Asp-Asp-Lys, SEQ ID NO:13). The fusion protein will not be exposed to Factor Xa so that the fraction of molecules having an ED peptide can be tracked when test animals are treated with the therapeutic protein agent.

Colonies grown on plates containing X-gal (5-bromo-4-chloro-3-indolyl-β-D-galactoside) that express proteins with amber-ED tracers should turn blue. Although the proteins expressed from pMAL-p2X are transported to the periplasm, blue coloration is typically observed.

EXAMPLE 2 pWKK-501

The plasmid pWKK-501 is constructed by digesting pWKK-500 with XbaI restriction endonuclease, filling in the resulting 5' sticky ends, and ligating the resulting blunt ends. The ligated plasmid is then amplified in *E. coli* cells and purified according to procedures well known in the art. Screening of candidates should include the lack of susceptibility to being digested with XbaI, because the XbaI site of pWKK-500 (nucleotides 2418-2423 of SEQ ID NO:2) is destroyed. However, a BfaI site (CTAG recognition sequence) is duplicated and intact. Screening of candidates during the construction of pWKK-501 from pWKK-500 by PCR using the BZ (SEQ ID NO:15) and LT-1 (SEQ ID NO:16) primers results in amplification of a 305-bp fragment. Should imperfect filling of 5' overhangs result in no BfaI site at the ligation junction, digestion of the 305-bp fragment with BfaI would result in generation of a DNA fragment of about 280 bp because of BfaI sites near each end of the fragment. If the BfaI sites are intact at the ligation junction, however, this fragment will not appear. Instead, fragments of about 80 bp and 200 bp will be formed.

The differences in the functional elements of pWKK-501 compared to those of pWKK-500 are as follows. After the hydrophilic linker (out-of-frame buforin), the lacZα peptide (ED), (His)$_6$ tag, and TGA stop codon are still present, but are in a different reading frame than in pWKK-500. That is, in pWKK-501 these elements are in the same reading frame as buforin and are out-of-frame with respect to the MBP-containing fusion protein. Therefore, in pWKK-501, buforin and ED are in the same reading frame and are separated by a TAG codon. Thus, pWKK-501 can serve as a starting plasmid for construction of other constructs, including those permitting amber-ED structures.

EXAMPLE 3 pWKK-502

The plasmid pWKK-502 is constructed by digesting plasmid pWKK-501 with BamHI restriction endonuclease and then religating the digested plasmid. A BamHI restriction site is preserved across the ligation junction. SpeI, AflII, and BbvCI restriction sites are destroyed in the process of constructing the plasmid.

The order of functional elements in pWKK-502 is as follows: MBP, Factor Xa site, myristylation signal, DP178, flexible linker, ricin A chain, HIV protease cleavable linker, ricin B chain (truncated), buforin II, amber (TAG) stop codon, lacZα peptide (ED), (His)$_6$ tag, TGA stop codon.

EXAMPLE 4 pWKK-503

The plasmid pWKK-503 is constructed by digesting plasmid pWKK-500 with AflII and NcoI restriction endonucleases, filling the resulting 5' cohesive ends with an appropriate DNA polymerase, and ligating the resulting blunt ends. A new BslI restriction site is created across the ligation junction, and the AflII and NcoI restriction sites are destroyed. Complete digestion of pWKK-500 with BslI will generate 20 DNA fragments, 16 of which are smaller than 380 bp in length. Only four large fragments of 846 bp, 904 bp, 1120 bp, and 1744 bp are expected. The 1744-bp fragment is produced by a BslI site near the SmaI/XmaI sites in the 5' end of the coding region for ricin A chain and a BslI site 350 bp beyond the BglI site just after the ED coding region. In the desired construct with the new BslI site, the 1744-bp fragment will be cut into a 947-bp fragment and a 779-bp fragment. These new fragments clearly distinguish the desired construct from undesirable ones. A double digestion with BslI and BglI confirms the construction of pWKK-503 by cutting the 779-bp fragment into 350-bp and 429-bp fragments. The 1120-bp fragment is also cut into 264-bp and 856-bp products. Double digestion with BslI and StyI specifically cuts the 947-bp fragment, yielding 267-bp and 680-bp fragments.

The order of functional elements in pWKK-503 is as follows: MBP, Factor Xa site, myristylation signal, DP178, flexible linker, ricin A chain, HIV protease cleavable linker, ricin B chain (truncated), repeat of hydrophobic stretch of ricin A chain, L domain motif, Factor Xa site, hydrophilic linker, lacZα peptide (ED), (His)$_6$ tag, TGA stop codon. Therefore, pWKK-503 is a derivative of pWKK-500 wherein the KDEL signal and amber stop codons have been removed.

EXAMPLE 5 pWKK-504

The plasmid pWKK-504 is constructed by digesting plasmid pWKK-501 with restriction endonucleases Acc65I and AflII, filling in the resulting 5' cohesive ends with DNA polymerase, and ligating the resulting blunt ends. An AflII restriction site is preserved across the ligation junction, but NcoI and Acc65I restriction sites are destroyed.

Plasmid pWKK-504 is a derivative of pWKK-500 wherein buforin II is at the C-terminus of the MBP-containing fusion protein. The order of functional elements in pWKK-504 is as follows: MBP, Factor Xa site, myristylation signal, DP178, flexible linker, ricin A chain, HIV protease cleavable linker, ricin B chain (truncated), repeat of hydrophobic stretch of ricin A chain, L domain motif, buforin II, amber (TAG) stop codon, lacZα peptide (ED), (His)$_6$ tag, TGA stop codon. The amber stop codon is followed by a non-optimal C residue, thus there is likely to be inefficient suppression of the amber codon in suppressor hosts.

EXAMPLE 6 pWKK-505

The plasmid pWKK-505 is constructed by digesting plasmid pWKK-502 with restriction endonuclease XmnI, then digesting with restriction endonuclease XbaI, digesting the cohesive end with a nuclease such as mung bean nuclease to result in blunt ends, and then ligating the resulting blunt ends. No restriction sites are preserved across the ligation junction, and the XmnI and XbaI restriction sites are destroyed.

An alternative method of preparing plasmid pWKK-505 involves digesting pWKK-502 with XmnI and XbaI, as described above, and then ligating a synthetic oligonucleotide into the digested plasmid. The synthetic oligonucleotide could contain a unique restriction site to facilitate plasmid screening. The synthetic oligonucleotide could be designed such that it contained an amber (TAG) stop codon that was efficiently suppressed in a suppressor strain and was in-frame with the ED coding sequence. One such potential synthetic oligonucleotide is CGGAAGTAGGCCT-NNNNNNNNNNTCTAGA (SEQ ID NO:17).

The order of functional elements present in pWKK-505 is as follows: MBP, Factor Xa site, myristylation signal, DP178, flexible linker, ricin A chain, HIV protease cleavable linker, ricin B chain (truncated), buforin II, amber (TAG) stop codon.

EXAMPLE 7 pWKK-506

The plasmid pWKK-506 is constructed by digesting pWKK-502 with restriction endonuclease Bsu36I, digesting the resulting cohesive ends with a nuclease such as mung bean nuclease to result in blunt ends, and then ligating the resulting blunt ends. Plasmid pWKK-506 could also be constructed by similarly digesting and ligating any of plasmids pWKK-500 through pWKK-505. The Bsu36I restriction site is destroyed, but a unique EagI restriction site is created across the ligation junction.

The order of functional elements in pWKK-506 is as follows: MBP, Factor Xa site, myristylation signal, DP178, flexible linker, ricin A chain, HIV protease cleavable linker, ricin B chain (truncated), buforin II, amber (TAG) stop codon, lacZα peptide (ED), (His)$_6$ tag, TGA stop codon. The ED peptide is in frame with the MBP-containing fusion protein. An advantage of this construct is that an extraneous leucine codon is removed from a Gly-Leu-Arg sequence, thereby resulting in a more natural buforin II amino acid sequence. The resulting Gly-Arg dipeptide, however, is likely to be more susceptible to Factor Xa digestion.

EXAMPLE 8 pWKK-507

The plasmid pWKK-507 is constructed by digesting pWKK-500 or pWKK-501 with AflII restriction endonuclease, filling in the resulting 5' cohesive ends with a suitable DNA polymerase, and then ligating the resulting blunt ends. The AflII site is destroyed, but a unique PacI site is created across the ligation junction and can be used for screening for correct construction of the plasmid.

Plasmid pWKK-507 has the KDEL signal deleted as compared to pWKK-500. Thus, the order of functional elements in pWKK-507 is as follows: MBP, Factor Xa site, myristylation signal, DP178, flexible linker, ricin A chain, HIV protease cleavable linker, ricin B chain (truncated), repeat of hydrophobic stretch of ricin A chain, L domain motif, TAA stop codon.

EXAMPLE 9 pWKK-508

The plasmid pWKK-508 is constructed by digesting plasmid pWKK-500 with restriction endonuclease AflII; filling in the resulting 5' cohesive ends with a DNA polymerase to produce blunt ends; then digesting the linearized, blunt-ended plasmid with restriction endonuclease MfeI; digesting the MfeI-digested plasmid with mung bean nuclease to remove the cohesive end and result in blunt ends; and ligating the blunt ends. The AflII restriction site is preserved across the ligation junction, however, MfeI, PstI, SpeI, and BbvCI sites are destroyed.

The order of functional elements in pWKK-508 is as follows: MBP, Factor Xa site, myristylation signal, DP178, flexible linker, ricin A chain, KDEL ER retention signal, amber (TAG) stop codon, Factor Xa site, hydrophilic linker, lacZα peptide (ED), (His)$_6$ tag, TGA stop codon. Therefore, pWKK-508 is a derivative of pWKK-500 wherein the KDEL ER retention signal is at the end of the ricin A chain portion of the fusion protein.

EXAMPLE 10 pWKK-509

The plasmid pWKK-509 is constructed by digesting plasmid pWKK-500 with restriction endonucleases MfeI and XbaI, filling in the resulting 5' cohesive ends with DNA polymerase, and ligating the blunt ends to result in an intermediate plasmid. The XbaI site is preserved in the intermediate plasmid, and this feature can be used in screening for the correct intermediate plasmid. This intermediate plasmid treated by digesting with restriction endonuclease XbaI, filling in the resulting 5' cohesive ends with DNA polymerase, and then ligating the resulting blunt ends to result in the plasmid pWKK-509. The following restriction sites are destroyed in the course of constructing the plasmid: MfeI, XmnI, PstI, SpeI, BamHI, NcoI, Acc65 I, Bsu36 I, AflII, BbvCI, and XbaI.

The order of functional elements of pWKK-509 is as follows: MBP, Factor Xa site, myristylation signal, DP178, flexible linker, ricin A chain, amber (TAG) stop codon, lacZα peptide (ED), (His)$_6$ tag, TGA stop codon. The coding sequence for the ED peptide is in frame with the coding sequence for the MBP-containing fusion protein. Therefore, this derivative of pWKK-500 expresses a fusion protein with an amber-ED tracer or a stop at the end of the ricin A chain portion thereof.

EXAMPLE 11 pWKK-510

The plasmid pWKK-510 is constructed by digesting plasmid pWKK-501 with restriction endonucleases BsrGI and Acc65I and then ligating the resulting compatible cohesive ends. The following restriction sites are destroyed: MfeI, BsrGI, PstI, SpeI, BamHI, NcoI, Acc65I, AflII, and BbvCI.

The order of functional elements encoded by pWKK-510 is as follows: MBP, Factor Xa site, myristylation signal, DP178, flexible linker, ricin A chain, buforin II, amber (TAG) stop codon, lacZα peptide (ED), (His)$_6$ tag, TGA stop codon. The non-optimal environment of the amber stop codon may result in inefficient suppression of the amber codon in suppressor strains. The fusion protein expressed from pWKK-510 comprises the MBP-containing fusion protein with buforin II and the amber-ED tracer at the end of the ricin A chain.

EXAMPLE 12 pWKK-511

The plasmid pWKK-511 is constructed by digesting plasmid pWKK-500 with restriction endonuclease BamHI, filling in the resulting 5' cohesive ends with DNA polymerase, and then ligating the resulting blunt ends. A new ClaI restriction site is created across the ligation junction, and the following restriction sites are destroyed: BamHI, SpeI, AflII, and BbvCI. Plasmid pWKK-500 has one ClaI site located in the ricin A chain coding sequence. The new ClaI site created across the ligation junction of pWKK-511 is 516 bp from the other ClaI site. The 516-bp ClaI fragment can be detected upon restriction fragment analysis. Since ClaI is sensitive to overlapping dam methylation, it is necessary to amplify the plasmid in a dam$^B$ strain.

EXAMPLE 13 pWKK-512

The plasmid pWKK-512 is constructed by digesting pWKK-501 with restriction endonucleases BamHI and XmnI, filling in the resulting 5' cohesive ends produced by the BamHI digestion with DNA polymerase, and then ligating the resulting blunt ends. A BstYI restriction site is preserved across the ligation junction. The following restrictions sites, however, are destroyed: SpeI, BamHI, AflII, BbvCI, NcoI, Acc65I, Bsu36I, and XmnI. BstYI digestion of pWKK-512 produces 12 fragments, 5 of which are less than 90 bp in length and not readily observable by standard agarose gel electrophoresis. Four of the fragments are within the pMAL-p2X vector sequence and have lengths of 2216 bp, 547 bp, 1263 bp, and 1451 bp. Three of the fragments include portions of the reading frame: 962 bp (5' end of the ricin A chain coding sequence), 256 bp (from BstYI sites near the BglII site to the new BstYI site at the ligation junction), and 1042 bp (from the new site at the ligation junction to a BstYI site 676 residues beyond the BglI site after the ED coding sequence). The 1042 bp fragment clearly indicates the presence of the desired construction. To confirm obtaining of pWKK-512, double digestion with BglI and BstYI cuts the 1042 bp fragment into 676 bp and 366 bp fragments. The 1263-bp fragment is also digested into 751-bp and 512-bp fragments. For comparison, digestion of pWKK-501 with BstYI yields a 1114-bp fragment instead of a 1042-bp fragment.

The fusion protein produced by expression of pWKK-512 is truncated after the ricin B chain. Thus, the order of functional elements in pWKK-512 is as follows: MBP, Factor Xa site, myristylation signal, DP178, flexible linker, ricin A chain, HIV protease cleavable linker, ricin B chain (truncated), amber (TAG) stop codon, lacZα peptide (ED), $(His)_6$ tag, TGA stop codon. The amber stop codon is in an environment, with a C residue following the TAG codon, which is not optimal for efficient suppression in suppressor strains.

EXAMPLE 14 pWKK-513

The plasmid pWKK-513 was constructed by digesting plasmid pWKK-500 with restriction endonucleases SpeI and XbaI and then ligating the resulting compatible cohesive ends. The following restriction sites are destroyed in this construction: SpeI, XbaI, AflII, BbvCI, NcoI, Acc65I, Bsu36I, and XmnI.

Plasmid pWKK-513 encodes a fusion protein similar to that of pWKK-511, but without the second Factor Xa site. Thus, the order of functional elements in pWKK-513 is as follows: MBP, Factor Xa site, myristylation signal, DP178, flexible linker, ricin A chain, HIV protease cleavable linker, ricin B chain (truncated), lacZα peptide (ED), $(His)_6$ tag, TGA stop codon.

EXAMPLE 15 pWKK-514

The plasmid pWKK-514 is constructed by digesting plasmid pWKK-500 with restriction endonucleases Acc65I and BbvCI, filling in the resulting 5' cohesive ends with DNA polymerase, and ligating the resulting blunt ends. The following restriction sites are destroyed in making the construct: NcoI, AflII, BbvCI, and Acc65I.

Thus, the order of functional elements encoded by plasmid pWKK-514 is as follows: MBP, Factor Xa site, myristylation signal, DP178, flexible linker, ricin A chain, HIV protease cleavable linker, ricin B chain (truncated), repeat of hydrophobic stretch of ricin A chain, Factor Xa site, hydrophilic linker, lacZα peptide (ED), $(His)_6$ tag, TGA stop codon. Thus, pWKK-514 is a derivative of pWKK-500 wherein a Factor Xa site-ED is appended to the fusion protein following the repeat of hydrophobic stretch of ricin A chain.

EXAMPLE 16 pWKK-515

The plasmid pWKK-515 was constructed by digesting plasmid pWKK-500 with restriction endonucleases MfeI and EcoRI and then ligating the resulting compatible cohesive ends. The following restriction sites were destroyed in making this construct: MfeI, PstI, BamHI, SpeI, BbvCI, AflII, NcoI, Acc65I, Bsu36I, XbaI, XmnI, and EcoRI.

Plasmid pWKK-515 is a derivative of pWKK-500 wherein a $(His)_6$ tag is attached to the fusion protein following the ricin A chain. Thus, the order of functional elements is as follows: MBP, Factor Xa site, myristylation signal, DP178, flexible linker, ricin A chain, $(His)_6$ tag, TGA stop codon.

EXAMPLE 17 pWKK-516

The plasmid pWKK-516 is constructed by digesting plasmid pWKK-500 with restriction endonucleases BbvCI and SpeI, filling in the resulting 5' cohesive ends with a DNA polymerase, and then ligating the resulting blunt ends. The SpeI site is preserved across the ligation junction, but the BbvCI site is destroyed.

Plasmid pWKK-516 is a derivative of pWKK-500 wherein a stop codon is placed after the truncated ricin B chain. Thus, the order of functional elements in pWKK-516 is as follows: MBP, Factor Xa site, myristylation signal, DP178, flexible linker, ricin A chain, HIV protease cleavable linker, ricin B chain (truncated), TAA stop codon.

EXAMPLE 18 pWKK-517

The plasmid pWKK-517 is constructed by digesting plasmid pWKK-500 with restriction endonucleases AflII and SpeI, filling in the resulting 5' cohesive ends with a DNA polymerase, and then ligating the resulting blunt ends. The SpeI site is preserved across the ligation junction, but a BbvCI site is destroyed.

Plasmid pWKK-517 is a derivative of pWKK-500 wherein the KDEL ER retention signal is placed after the truncated ricin B chain. Thus, the order of functional elements in pWKK-517 is as follows: MBP, Factor Xa site, myristylation signal, DP178, flexible linker, ricin A chain, HIV protease cleavable linker, ricin B chain (truncated), KDEL ER retention signal, amber (TAG) stop codon, Factor Xa site, hydrophilic linker, lacZα peptide (ED), $(His)_6$ tag, TGA stop codon.

EXAMPLE 19 pWKK-518

The plasmid pWKK-518 is constructed by digesting plasmid pWKK-500 with restriction endonucleases BbvCI and SpeI, digesting the resulting 5' cohesive ends with an exonuclease such as mung bean nuclease such that blunt ends are obtained, and then ligating the blunt ends. A Cac8I restriction site is created across the ligation junction, but the BbvCI and SpeI sites are destroyed. Complete digestion of pWKK-518 with Cac8I results in 45 fragments, of which 31 fragments are less than 200 bp in length, 9 fragments are between 200 and 400 bp in length, and 5 fragments are greater than 400 bp in length (i.e., 865 bp, 613 bp, 844 bp, 560 bp, and 456 bp). The 865-bp fragment includes the ricin A chain coding sequence from a site near the N terminus of the ricin A chain proper to the site created at the ligation junction. This is the distinctive fragment for confirming proper construction of the plasmid and is the largest fragment generated, however, it is close in size to the 844-bp fragment. The 844-bp and 613-bp fragments are digested by DraI, but the 865-bp fragment is not. The 865-bp fragment, however, is digested with ClaI into 525-bp and 340-bp fragments. In contrast, pWKK-500 yields a 1132-bp fragment instead of an 865-bp fragment when digested with Cac8I.

Plasmid pWKK-518 is a derivative of pWKK-500 wherein the L domain motif and KDEL ER retention signal are after the truncated ricin B chain. Thus, the order of functional elements is as follows: MBP, Factor Xa site, myristylation signal, DP178, flexible linker, ricin A chain, HIV protease cleavable linker, ricin B chain (truncated), L domain motif, KDEL ER retention signal, amber (TAG) stop codon, Factor Xa site, hydrophilic linker, lacZα peptide (ED), (His)$_6$ tag, TGA stop codon.

EXAMPLE 20 pWKK-519

The plasmid pWKK-519 is constructed by digesting plasmid pWKK-500 with restriction endonuclease BsiWI, and then ligating the resulting compatible cohesive ends. There are two BsiWI sites in pWKK-500, and removing the smaller fragment of about 822 bp results in pWKK-519. A BsiWI restriction site is preserved across the ligation junction, but a SacI restriction site is destroyed.

Plasmid pWKK-519 is a derivative of pWKK-500 wherein the MBP coding sequence is truncated. Thus, the order of functional elements of pWKK-519 is as follows: MBP (truncated), Factor Xa site, myristylation signal, DP178, flexible linker, ricin A chain, HIV protease cleavable linker, ricin B chain (truncated), repeat of hydrophobic stretch of ricin A chain, L domain motif, KDEL ER retention signal, amber (TAG) stop codon, Factor Xa site, hydrophilic linker (out-of-frame buforin), lacZα peptide (ED), (His)$_6$ tag, TGA stop codon. The signal peptide for periplasmic secretion in retained in the truncated MBP.

EXAMPLE 21 pWKK-520

The plasmid pWKK-520 is constructed by partially digesting plasmid pWKK-500 with restriction endonuclease NdeI such that only one of the two NdeI sites is cut in a majority of plasmids, filling in the resulting 5' cohesive ends with a DNA polymerase, digesting the resulting polished ends with restriction endonuclease SnaBI, and then ligating the blunt ends. The ligated DNA is then digested with restriction endonuclease SacI to linearize plasmids that were cut at the wrong NdeI site (within the ricin A chain coding sequence) or that were not cut at all by NdeI. After amplification in bacteria, candidate plasmids are screened for susceptibility to digestion with SphI, which is present in the correctly made construct but not in other constructs. Restriction sites destroyed in making the construct include SacI, SnaBI, and BsiWI.

Plasmid pWKK-520 is a derivative of pWKK-500 wherein there is no maltose binding protein in the fusion protein expressed by the plasmid. The order of functional elements in pWKK-520 is as follows: Factor Xa site, myristylation signal, DP178, flexible linker, ricin A chain, HIV protease cleavable linker, ricin B chain (truncated), repeat of hydrophobic stretch of ricin A chain, L domain motif, KDEL ER retention signal, amber (TAG) stop codon, Factor Xa site, hydrophilic linker (out-of-frame buforin), lacZα peptide (ED), (His)$_6$ tag, TGA stop codon.

EXAMPLE 22 pWKK-700

The plasmid pWKK-700 was created by inserting a synthetic oligonucleotide of about 250 bp encoding the RANTES chemokine into plasmid pWKK-500 digested with restriction endonucleases SacI and AgeI. The sequence of the region of pWKK-700 coding for the fusion protein is disclosed as SEQ ID NO:20. The RANTES-encoding synthetic oligonucleotide was prepared by annealing oligonucleotides OC-1 (75-mer, SEQ ID NO:21) and OC-2 (72-mer, SEQ ID NO:22) to OC-5 (46-mer, SEQ ID NO:23) so that OC-1 and OC-2 could be ligated to create one continuous strand. This strand was amplified by PCR using oligonucleotides OC-3 (forward primer, SEQ ID NO:24) and OC-4 (reverse primer, SEQ ID NO:25). The PCR product was gel purified, digested with restriction endonucleases SacI and AgeI and then ligated to the similarly digested pWKK-500.

CCR5 is a chemokine co-receptor for HIV entry into cells. RANTES (regulated on activation, normal T-cell expressed and secreted) is a natural ligand to CCR5. The sequence of RANTES encoded by pWKK-700 is SEQ ID NO:39. Use of RANTES as a targeting moiety directs the therapeutic agent to cells susceptible to infection. HIV protease activates the agent so that only infected cells are killed. E. Gonzalez et al., Global survey of genetic variation in CCR5, RANTES, MIP-1alpha: impact on the epidemiology of the HIV-1 pandemic, 98 Proc. Nat=1 Acad. Sci. USA 5199-5204 (2001).

Modification of the N terminus of RANTES by the addition of a single amino acid, methionine, converts the proinflammatory cytokine into an antagonist, which lacks the activities of normal RANTES. Indeed, the modified M-RANTES apparently binds to the same receptor that binds to RANTES, thereby blocking RANTES-induced signaling pathways. Since the use of RANTES as a targeting moiety could lead to unwanted effects caused by its cytokine activities, the availability of recombinant toxins targeted by N-terminally modified RANTES is desirable. It is assumed that other amino acids, or very short polymers thereof, would have a similar antagonistic effect when appended to the N-terminus of RANTES. The plasmid pWKK-700 encodes a RANTES variant with an aspartate-methionine dipeptide appended to the natural N-terminus of RANTES and immediately following the Factor Xa cleavage site. This particular embodiment permitted the inclusion of unique restriction sites that enable the deletion of the dipeptide-encoding DNA segment to produce a natural N-terminus, which is encoded in pWKK-721. A. E. Proudfoot et al., Extension of recombinant human RANTES by the retention of the initiating methionine produces a potent antagonist, 271 J. Biol. Chem. 2599-2603 (1996).

The order of functional elements in pWKK-700 is as follows: MBP, Factor Xa site, RANTES, flexible linker, ricin A chain, HIV protease cleavable linker (SEQ ID NO:8), ricin B chain (truncated), repeat of hydrophobic stretch of ricin A chain, L domain motif, KDEL ER retention signal, amber (TAG) stop codon, Factor Xa site, hydrophilic linker (out-of-frame buforin), lacZα peptide (ED), $(His)_6$ tag, TGA stop codon.

EXAMPLE 23 pWKK-701 Through pWKK-720

Plasmids pWKK-701 through pWKK-720 are derivatives of pWKK-700 prepared in a manner analogous to the manner that pWKK-501 through pWKK-520 are prepared as derivatives of pWKK-500.

EXAMPLE 24 pWKK-721

The plasmid pWKK-721 is constructed by digesting plasmid pWKK-700 with restriction endonuclease PshAI, then digesting the PshAI-digested plasmid with NruI, and then ligating the resulting blunt ends. The NruI and PshAI restriction sites are destroyed in the process of making the construct.

Plasmid pWKK-721 is a derivative of pWKK-700 wherein the RANTES portion of the fusion protein has a natural N-terminal sequence. The order of functional elements in pWKK-721 is the same as in pWKK-700.

EXAMPLE 25 pWKK-722

The plasmid pWKK-722 is constructed by partially digesting plasmid pWKK-700 with NdeI such that only one of the two NdeI sites is cut in a majority of plasmids, filling in the 5' cohesive ends with a DNA polymerase to produce blunt ends, digesting the blunt-ended plasmid DNA with restriction endonuclease NruI, and then ligating the resulting blunt ends. The ligated DNA is then digested with SacI to linearize recircularized plasmids that were cut at the wrong NdeI site (i.e., within the coding sequence for the ricin A chain) or that were not cut at all by NdeI. The SacI-digested DNA is then used to transform *E. coli* cells, pick colonies, and prepare candidate plasmids for screening. Plasmids are then screened for susceptibility to SphI, which indicates the correct construction. Restriction sites destroyed in the process of constructing this plasmid include SacI, NruI, and BsiWI.

Plasmid pWKK-722 is a derivative of pWKK-700 wherein the maltose binding protein coding sequence is removed. Therefore, the order of functional elements in pWKK-722 is as follows: RANTES, flexible linker, ricin A chain, HIV protease cleavable linker, ricin B chain (truncated), repeat of hydrophobic stretch of ricin A chain, L domain motif, KDEL ER retention signal, amber (TAG) stop codon, Factor Xa site, hydrophilic linker (out-of-frame buforin), lacZα peptide (ED), $(His)_6$ tag, TGA stop codon.

EXAMPLE 26 pWKK-800

The plasmid pWKK-800, the coding sequence of which is disclosed as SEQ ID NO:26, was constructed by inserting a synthetic oligonucleotide of about 275 bp encoding the SDF-1 chemokine into pWKK-500 digested with restriction endonucleases SacI and SphI to eliminate the DP178-encoding segment. The SDF-1-encoding fragment was prepared from synthetic oligonucleotides using a nested PCR approach. First, oligonucleotides AB-2 (inner reverse primer, SEQ ID NO:27), AB-3 (mid template, SEQ ID NO:28), and AB-5 (inner forward primer, SEQ ID NO:29) were used for 5 cycles of PCR. Then, oligonucleotides AB-1 (outer reverse primer, SEQ ID NO:30) and AB-4 (outer forward primer, SEQ ID NO:31) were added and PCR was resumed. After amplification was completed, the PCR product was gel purified and digested with restriction endonucleases SacI and SphI. The digested PCR product was then ligated to similarly digested pWKK-500.

CXCR4 is a chemokine co-receptor for HIV entry into cells. SDF-1 (stromal cell-derived factor-1) is a natural ligand to CXCR4. Use of SDF-1 as a targeting moiety directs the therapeutic agent to cells susceptible to infection. The sequence of SDF-1 as encoded by pWKK-800 is SEQ ID NO:40. HIV protease activates the agent such that only infected cells are killed. J. Di Salvo et al., The CXCR4 agonist ligand stromal derived factor-1 maintains high affinity for receptors in both Galpha(i)-coupled and uncoupled states, 409 Eur. J. Pharmacol. 143-154 (2000). Truncated versions of SDF-1 that include N-terminal sequences of the peptide show receptor binding activity. Accordingly, pWKK-821 encodes a truncated version of SDF-1. E. L. Elisseeva et al., NMR studies of active N-terminal peptides of stromal cell derived factor-1. Structural basis for receptor binding, 275 J. Biol. Chem. 26799-26805 (2000).

The order of functional elements in pWKK-800 is as follows: MBP, Factor Xa site, SDF-1, flexible linker, ricin A chain, HIV protease cleavable linker (SEQ ID NO:8), ricin B chain (truncated), repeat of hydrophobic stretch of ricin A chain, L domain motif, KDEL ER retention signal, amber (TAG) stop codon, Factor Xa site, hydrophilic linker (out-of-frame buforin), lacZα peptide (ED), $(His)_6$ tag, TGA stop codon.

EXAMPLE 27 pWKK-801 Through pWKK-820

Plasmids pWKK-801 through pWKK-820 are derivatives of pWKK-800 prepared in a manner analogous to the manner that pWKK-501 through pWKK-520 are prepared as derivatives of pWKK-500.

EXAMPLE 28 pWKK-821

The plasmid pWKK-821 is constructed by digesting plasmid pWKK-800 with restriction endonucleases PmlI and PshAI and then ligating the resulting blunt ends. A unique AgeI site is created across the ligation junction, but the PmlI and PshAI sites are destroyed in the course of construction of the plasmid.

Plasmid pWKK-821 is a derivative of pWKK-800 wherein SDF-1 is truncated. Thus, the order of functional elements in pWKK-821 is the same as in pWKK-800 except that a truncated SDF-1 replaces SDF-1. The sequence of the truncated version of SDF-1 is SEQ ID NO:41.

EXAMPLE 29 pWKK-900

The plasmid pWKK-900 is constructed by inserting a synthetic oligonucleotide encoding a potential lethal factor-cleavable peptide linker into pWKK-500 digested with MfeI and PstI to eliminate the HIV protease cleavable linker.

T-20, also known as DP178, is a known ligand/agonist of the phagocyte N-formyl peptide receptor (FPR) and of the similar FPR-like 1 receptor (FPRL1R), which occur in monocytes and macrophages derived therefrom. Lethal factor (LF) is a protease that cleaves a defined sequence (Pro-Lys-Lys-Lys-Pro-Thr-Pro-Ile-Gln-Leu-Asn-Pro-Ala, SEQ ID NO:32) at the N-terminus of mitogen-activated protein kinase kinase 1 (MAPKK1) and similar regulatory enzymes. This activity may occur on a similar sequence integrated into a potential therapeutic agent, thereby activating the ricin-based agent. LF causes macrophages to secrete inflammatory chemokines (e.g., tumor necrosis factor-alpha), inducing systemic shock and death.

In advanced cases of inhalational anthrax, death is probable despite antibiotic therapy, because bacterially produced toxins in the system are unaffected by antibiotics. Theoretically, a therapeutic agent that selectively eliminates compromised immune cells (i.e., intoxicated by LF) could reduce systemic shock by reducing the amounts of chemokines secreted into the system. The protein agent encoded by pWKK-900 contains DP178, which directs binding of the agent to immune cells that may be potentially compromised (i.e., monocytes and macrophages). However, the agent should be activated only in cells that contain LF, thereby sparing healthy cells. N. S. Duesberry et al., Proteolytic inactivation of MAP-kinase-kinase by anthrax lethal factor, 280 Science 734-737 (1998); J. K. Hartt et al., The HIV-1 cell entry inhibitor T-20 potently chemoattracts neutrophils by specifically activating the N-formylpeptide receptor, 272 Biochem. Biophys. Res. Commun. 699-704 (2000); P. C. Hanna et al., Role of macrophage oxidative burst in the action of anthrax lethal toxin, 1 Mol. Med. 7-18 (1994); D. Yang et al., Differential regulation of formyl peptide receptor-like 1 expression during the differentiation of monocytes to dendritic cells and macrophages, 166 J. Immunol. 4092-4098 (2001).

Preparation of pWKK-900 comprises digesting pWKK-500 with restriction endonucleases MfeI and PstI, ligating a synthetic cassette having MfeI- and PstI-compatible cohesive ends formed by annealing an upper oligonucleotide (SEQ ID NO:33) and a lower oligonucleotide (SEQ ID NO:34), transforming competent E. coli cells and screening plasmid candidates with restriction endonuclease BglI to determine if the cassette is in place, and verifying that the ligation junctions are correct by digestion with MfeI and PstI.

The order of functional elements in pWKK-900 is as follows: MBP, Factor Xa site, myristylation signal, DP178, flexible linker, ricin A chain, Lethal Factor protease cleavable linker, ricin B chain (truncated), repeat of hydrophobic stretch of ricin A chain, L domain motif, KDEL ER retention signal, amber (TAG) stop codon, Factor Xa site, hydrophilic linker (out-of-frame buforin II), lacZα peptide (ED), (His)$_6$ tag, TGA stop codon.

EXAMPLE 30 pWKK-901 Through pWKK-920

Plasmids pWKK-901 through pWKK-920 are derivatives of pWKK-900 prepared in a manner analogous to the manner that pWKK-501 through pWKK-520 are prepared as derivatives of pWKK-500.

EXAMPLE 31 pWKK-21

The plasmid pWKK-21 (SEQ ID NO:35) is constructed by digesting plasmid pWKK-15 (SEQ ID NO:37) with restriction endonucleases SacI and AgeI and ligating a cassette formed by annealing synthetic oligonucleotides with compatible ends into the digested plasmid. This construction replaced the Factor Xa/myristylation signal/DP 178 sequence of pWKK-15 with a Factor Xa/concealed myristylation signal sequence/one-domain ricin B chain. Candidate plasmids were screened by digestion with restriction endonuclease SalI.

With each of the two domains of the ricin B chain containing three subdomains, the DNA encoding these subdomains was rearranged such that the first subdomain (1 alpha) and the last subdomain of the second domain (2 gamma) were connected by a hybrid interceding domain (1 beta/12 beta). Since galactose-binding sites occur in the 1 alpha and 2 gamma subdomains, this one-domain B chain contains at least two potential galactose-binding sites. Further, minimization of the size of the B chain without compromising its galactose-binding function serves to facilitate translocation of the construct into cells. A. E. Frankel et al., Ricin toxin contains at least three galactose-binding sites located in B chain subdomains 1 alpha, 1 beta, and 2 gamma, 35 Biochemistry 14749-14756 (1996).

The rationale for making pWKK-21 is that the one-domain ricin B chain should retain its ability to bind to galactosyl moieties on a cell surface. Most, if not all, cell types have such moieties. Therefore, the 1-domain ricin B chain simply provides a means of attachment to cells, while the HIV protease cleavable linker provides selectivity for HIV-infected cells.

The order of functional elements in pWKK-21 is as follows: MBP, Factor Xa site, concealed myristylation signal, flexible linker, ricin A chain, protease cleavable linker (SEQ ID NO:8), 1-domain ricin B chain, repeat of hydrophobic stretch of ricin A chain, L domain motif, KDEL ER retention signal, stop codon.

EXAMPLE 32 pWKK-21a

The plasmid pWKK-21a is made by digesting pWKK-21 with restriction endonucleases NheI and XbaI and then ligating the resulting compatible cohesive ends. This construction places the lacZα peptide (ED) of β-galactosidase immediately after the 1-domain ricin B chain. The repeat of hydrophobic stretch of ricin A chain, the L domain motif, and the KDEL signal are deleted.

EXAMPLE 33 pWKK-21b

The plasmid pWKK-21b is made by digesting pWKK-21 with restriction endonucleases SalI and XhoI, then ligating the resulting compatible cohesive ends. This construction places the myristylation signal immediately after the Factor Xa site. This permits a functional myristylation signal. In the fusion protein encoded by pWKK-21, with a Leu-Ser-Arg sequence between the Factor Xa site and the myristylation signal site, cleavage with Factor Xa will not expose a functional myristylation signal.

EXAMPLE 34 pWKK-21c

The plasmid pWKK-21c is made by digesting pWKK-21 with restriction endonuclease AflII at the two sites for this restriction endonuclease and religating the digested plasmid. This construction deletes the L domain motif and the repeat of hydrophobic stretch of ricin A chain.

EXAMPLE 35 pWKK-21d

The plasmid pWKK-21d is made by digesting pWKK-21 with AflII, filling in the resulting 5' cohesive ends with a DNA polymerase to obtain blunt ends, and then ligating the blunt ends. This construction places a TAA stop codon after the 1-domain ricin B chain. A unique PacI site is created across the ligation junction to facilitate screening of candidate plasmids.

EXAMPLE 36

HIV Protease-Cleavable Linker Cassette

An oligonucleotide cassette encoding an HIV protease-cleavable linker was constructed having the sequence set out in SEQ ID NO:36, which encodes the peptide sequence set out in SEQ ID NO:8. Thus, the cassette will permit digestion of the resulting fusion protein by HIV protease. The oligonucleotide cassette occurs in plasmids pWKK-15 (SEQ ID NO:37), pWKK-21 (SEQ ID NO:35), pWKK-500 (SEQ ID NO:2), pWKK-700 (SEQ ID NO:20), and pWKK-800 (SEQ ID NO:26). The cassette is bounded by unique MfeI and PstI restriction sites to facilitate its removal and exchange with an alternative cassette. The cassette can be made by oligonucleotide synthesis according to methods well known in the art.

EXAMPLE 37

Alternative HIV Protease-Cleavable Linker Cassette

An alternative HIV protease-cleavable linker cassette is constructed by annealing oligonucleotides having the sequences set out in SEQ ID NO:18 and SEQ ID NO:19. These oligonucleotides can be made by oligonucleotide synthesis, as is well known in the art. Upon ligation of the cassette resulting from annealing of the oligonucleotides into pWKK-500 digested with MfeI and PstI restriction endonucleases, the MfeI site is preserved, the PstI site is destroyed, and a new BsrDI site is created to facilitate screening of plasmid candidates. For a plasmid derived from pWKK-500, complete digestion with BsrDI results in 5 DNA fragments of 366 bp, 174 bp, 2897 bp, 2979 bp, and 1638 bp. The 1638-bp fragmentB the diagnostic fragmentB arises from the new site introduced in the cassette and another BsrDI site to the 3' side in the coding strand, the introduced BsrDI site also contributes to generation of the 2897-bp fragment.

The cassette encodes an alternative HIV protease-cleavable peptide linker (Ser-Ala-Thr-Ile-Met-Met-Gln-Arg-Gly-Asn; SEQ ID NO:42). Thus, inserting the cassette into a construct encoding a fusion protein will permit digestion of the resulting fusion protein by HIV protease.

EXAMPLE 38

Multiple Derivatives of pWKK-500

Examples 2-21 describe derivatives of pWKK-500 made by recombinant DNA technology to result in plasmids pWKK-501 through pWKK-520. Additional derivatives of pWKK-500 are made by sequentially performing more than one of the manipulations described in Examples 2-21. Some of the manipulations described in these examples, however, are mutually exclusive, as will be described in more detail below. For example, manipulations of DNA encoding C-terminal segments of the expressed proteins will generally be mutually exclusive, as will manipulations of the DNA encoding MBP, terminal targeting moieties, and buforin II.

For convenience in referring to the steps for forming the various multiple-derivative plasmids, the steps for making pWKK-501 from pWKK-500 will be referred to herein as "the 501 derivation" or "derivation 501," the steps for making pWKK-502 from pWKK-500 will be referred to as "the 502 derivation" or "derivation 502," and so forth. Therefore, according to the present example, multiple-derivative plasmids are made starting with pWKK-500 and performing (a) any one of the derivations selected from the group consisting of derivations 501 through 518, and (b) either the 519 or the 520 derivation. An illustrative example of such a multiple-derivative plasmid is a plasmid made by starting with pWKK-500 and performing the 501 and 519 derivations to it. These derivations can be performed to pWKK-500 in either order. Another illustrative example of such a multiple-derivative plasmid is a plasmid made by starting with pWKK-500 and performing the 520 and 518 derivations to it.

EXAMPLE 39

Additional Multiple Derivatives pWKK-500

Additional derivatives of pWKK-500 are made by starting with plasmid pWKK-500 and then performing two or more of: (a) the 501 derivation, (b) the 502 or 504 or 510 derivation, (c) the 505 derivation, with the proviso that the 501 derivation must be omitted, (d) the 506 derivation, and (e) the 519 or 520 derivation. Accordingly, an illustrative derivative of pWKK-500 is made by performing the 504, 520, and 506 derivations.

EXAMPLE 40

Multiple Derivatives of pWKK-700

Examples 23-25 describe derivatives of pWKK-700 made by recombinant DNA technology to result in plasmids pWKK-701 through pWKK-722. Additional derivatives of pWKK-700 are made by sequentially performing more than one of the manipulations described in Examples 23-25. Some of the manipulations described in these examples, however, are mutually exclusive, as will be described in more detail below.

For convenience in referring to the steps for forming the various multiple-derivative plasmids, the steps for making pWKK-701 from pWKK-700 will be referred to herein as the 701 derivation, the steps for making pWKK-702 from pWKK-700 will be referred to as the 702 derivation, and so forth. Additional derivatives of pWKK-700 are made by starting with plasmid pWKK-700 and then performing two or more of: (a) any one of the derivations selected from the group consisting of derivations 701 through 718, (b) the 721 derivation, and (c) the 719 or 720 or 722 derivation, with the proviso that the 721 derivation cannot precede the 722 derivation.

EXAMPLE 41

Additional Multiple Derivatives of pWKK-700

Additional derivatives of pWKK-700 are made by starting with plasmid pWKK-700 and then performing two or more of: (a) the 701 derivation, (b) the 702 or 704 or 710 derivation, (c) the 705 derivation, with the proviso that the 701 derivation must be omitted, (d) the 706 derivation, (e) the 719 or 720 or 722 derivation, with the proviso that the 721 derivation cannot be performed prior to the 722 derivation, and (f) the 721 derivation. Accordingly, an illustrative derivative of pWKK-700 is made by performing the 704, 720, and 706 derivations.

EXAMPLE 42

Multiple Derivatives of pWKK-800

Examples 27-28 describe derivatives of pWKK-800 made by recombinant DNA technology to result in plasmids pWKK-801 through pWKK-821. Additional derivatives of pWKK-800 are made by sequentially performing more than one of the manipulations described in Examples 27-28. Some of the manipulations described in these examples, however, are mutually exclusive, as will be described in more detail below.

For convenience in referring to the steps for forming the various multiple-derivative plasmids, the steps for making pWKK-801 from pWKK-800 will be referred to herein as the 801 derivation, the steps for making pWKK-802 from pWKK-800 will be referred to as the 802 derivation, and so forth. Additional derivatives of pWKK-800 are made by starting with plasmid pWKK-800 and then performing two or more of: (a) any one of the derivations selected from the group consisting of derivations 801 through 818, (b) the 821 derivation, and (c) the 819 or 820 derivation.

EXAMPLE 43

Additional Multiple Derivatives of pWKK-800

Additional derivatives of pWKK-800 are made by starting with plasmid pWKK-800 and then performing two or more of: (a) the 801 derivation, (b) the 802 or 804 or 810 derivation, (c) the 805 derivation, with the proviso that the 801 derivation must be omitted, (d) the 806 derivation, (e) the 819 or 820 derivation, and (f) the 821 derivation. Accordingly, an illustrative derivative of pWKK-800 is made by performing the 804, 820, and 806 derivations.

EXAMPLE 44

Multiple Derivatives of pWKK-21

Examples 32-35 describe derivatives of pWKK-21 made by recombinant DNA technology to result in plasmids pWKK-21a through pWKK-21d. Additional derivatives of pWKK-21 are made by sequentially performing more than one of the manipulations described in Examples 32-35. Some of the manipulations described in these examples, however, are mutually exclusive, as will be described in more detail below.

For convenience in referring to the steps for forming the various multiple-derivative plasmids, the steps for making pWKK-21a from pWKK-21 will be referred to herein as the 21a derivation, the steps for making pWKK-21b from pWKK-21 will be referred to as the 21b derivation, and so forth. Additional derivatives of pWKK-21 are made by starting with plasmid pWKK-21 and then performing: (a) derivation 21b, and (b) the 21a or 21c or 21d derivation.

The invention claimed is:

1. A plasmid encoding an anti-HIV therapeutic agent comprising a fusion protein, wherein the fusion protein comprises a DP178 peptide as a targeting moiety and a ricin A chain as a polypeptide toxin, wherein the plasmid has a nucleotide sequence comprising SEQ ID NO:2.

2. An isolated polynucleotide comprising a sequence selected from the group consisting of:

(a) SEQ ID NO: 2; and
(b) the full complement of SEQ ID NO: 2.

3. An expression vector comprising the polynucleotide of claim 2 operably linked to an expression control sequence.

4. A host cell in culture transformed or transfected with an expression vector according to claim 3.

* * * * *

SEQUENCE LISTING

```
<160> NUMBER OF SEQ ID NOS: 43

<210> SEQ ID NO 1
<211> LENGTH: 6721
<212> TYPE: DNA
<213> ORGANISM: Artificial
<220> FEATURE:
<223> OTHER INFORMATION: Plasmid pMAL-p2X.

<400> SEQUENCE: 1
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
```

```
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatgcg ctgggcgcaa     840 tgcgcgccat taccgagtcc gggctgcgcg ttggtgcgga tatctcggta gtgggatacg    900
acgataccga agacagctca tgttatatcc gccgttaac caccatcaaa caggattttc      960
gcctgctggg gcaaaccagc gtggaccgct tgctgcaact ctctcagggc caggcggtga    1020
agggcaatca gctgttgccc gtctcactgg tgaaagaaa aaccaccctg gcgcccaata     1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt cgccgacat cataacggtt      1380 ctggcaaata ttctgaaatg agctgttgac aattaatcat cggctcgtat aatgtgtgga    1440
attgtgagcg ataacaatt tcacacagga acagccagt ccgtttaggt gttttcacga      1500
gcacttcacc aacaaggacc atagcatatg aaaataaaaa caggtgcacg catcctcgca    1560
ttatccgcat taacgacgat gatgttttcc gcctcggctc tcgccaaaat cgaagaaggt    1620
aaactggtaa tctggattaa cggcgataaa ggctataacg gtctcgctga agtcggtaag    1680
aaattcgaga aagataccgg aattaaagtc accgttgagc atccggataa actggaagag    1740
aaattcccac aggttgcggc aactggcgat ggccctgaca ttatcttctg gcacacgac     1800 cgctttggtg gctacgctca atctggcctg ttggctgaaa tcaccccgga caaagcgttc    1860
caggacaagc tgtatccgtt tacctgggat gccgtacgtt acaacggcaa gctgattgct    1920
tacccgatcg ctgttgaagc gttatcgctg atttataaca aagatctgct gccgaacccg    1980
ccaaaaacct gggaagagat cccggcgctg gataaagaac tgaaagcgaa aggtaagagc    2040
gcgctgatgt tcaacctgca agaaccgtac ttcacctggc cgctgattgc tgctgacggg    2100
ggttatgcgt tcaagtatga aaacggcaag tacgacatta aagacgtggg cgtggataac    2160
gctggcgcga aagcgggtct gaccttcctg gttgacctga ttaaaaacaa acacatgaat    2220
gcagacaccg attactccat cgcagaagct gcctttaata aaggcgaaac agcgatgacc    2280
atcaacggcc cgtgggcatg gtccaacatc gacaccagca agtgaatta tggtgtaacg    2340 gtactgccga ccttcaaggg tcaaccatcc aaaccgttcg ttggcgtgct gagcgcaggt    2400
attaacgccg ccagtccgaa caaagagctg gcaaaagagt cctcgaaaa ctatctgctg    2460 actgatgaag gtctggaagc ggttaataaa gacaaaccgc tgggtgccgt agcgctgaag    2520
tcttacgagg aagagttggc gaaagatcca cgtattgccg ccactatgga aaacgcccag    2580
aaaggtgaaa tcatgccgaa catcccgcag atgtccgctt ctggtatgc cgtgcgtact     2640 gcggtgatca acgccgccag cggtcgtcag actgtcgatg aagccctgaa agacgcgcag    2700
actaattcga gctcgaacaa caacaacaat aacaataaca caacctcgg gatcgaggga    2760 aggatttcag aattcggatc ctctagagtc gacctgcagg caagcttggc actggccgtc    2820
```

```
gttttacaac gtcgtgactg ggaaaaccct ggcgttaccc aacttaatcg ccttgcagca    2880
catccccctt tcgccagctg gcgtaatagc gaagaggccc gcaccgatcg cccttcccaa    2940
cagttgcgca gcctgaatgg cgaatggcag cttggctgtt ttggcggatg agataagatt    3000
ttcagcctga tacagattaa atcagaacgc agaagcggtc tgataaaaca gaatttgcct    3060
ggcggcagta gcgcggtggt cccacctgac cccatgccga actcagaagt gaaacgccgt    3120
agcgccgatg gtagtgtggg gtctccccat gcgagagtag ggaactgcca ggcatcaaat    3180
aaaacgaaag gctcagtcga aagactgggc ctttcgtttt atctgttgtt tgtcggtgaa    3240
cgctctcctg agtaggacaa atccgccggg agcggatttg aacgttgcga agcaacggcc    3300
cggagggtgg cgggcaggac gcccgccata aactgccagg catcaaatta gcagaaggc    3360 catcctgacg gatggccttt ttgcgtttct acaaactctt tttgtttatt tttctaaata    3420
cattcaaata tgtatccgct catgagacaa taaccctgat aaatgcttca ataatattga    3480
aaaaggaaga gtatgagtat tcaacatttc cgtgtcgccc ttattccctt ttttgcggca    3540
ttttgccttc ctgttttttgc tcacccagaa acgctggtga agtaaaaga tgctgaagat    3600 cagttgggtg cacgagtggg ttacatcgaa ctggatctca acagcggtaa gatccttgag    3660
agttttcgcc ccgaagaacg ttctccaatg atgagcactt ttaaagttct gctatgtggc    3720
gcggtattat cccgtgttga cgccgggcaa gagcaactcg gtcgccgcat acactattct    3780
cagaatgact tggttgagta ctcaccagtc acagaaaagc atcttacgga tggcatgaca    3840
gtaagagaat tatgcagtgc tgccataacc atgagtgata acactgcggc caacttactt    3900
ctgacaacga tcggaggacc gaaggagcta accgcttttt tgcacaacat ggggatcat    3960 gtaactcgcc ttgatcgttg ggaaccggag ctgaatgaag ccataccaaa cgacgagcgt    4020
gacaccacga tgcctgtagc aatggcaaca acgttgcgca aactattaac tggcgaacta    4080
cttactctag cttcccggca acaattaata gactggatgg aggcggataa agttgcagga    4140
ccacttctgc gctcggccct tccggctggc tggtttattg ctgataaatc tggagccggt    4200
gagcgtgggt ctcgcggtat cattgcagca ctggggccag atggtaagcc ctcccgtatc    4260
gtagttatct acacgacggg gagtcaggca actatggatg aacgaaatag acagatcgct    4320
gagataggtg cctcactgat taagcattgg taactgtcag accaagttta ctcatatata    4380
ctttagattg atttaccccg gttgataatc agaaaagccc caaaacagg aagattgtat    4440 aagcaaatat ttaaattgta acgttaata ttttgttaaa attcgcgtta aattttgtt    4500 aaatcagctc attttttaac caataggccg aaatcggcaa atcccttat aaatcaaaag    4560 aatagaccga ataggggttg agtgttgttc cagtttggaa caagagtcca ctattaaga    4620 acgtggactc caacgtcaaa gggcgaaaaa ccgtctatca gggcgatggc ccactacgtg    4680
aaccatcacc caaatcaagt tttttggggt cgaggtgccg taaagcacta atcggaacc    4740 ctaaagggag cccccgattt agagcttgac ggggaaagcc ggcgaacgtg cgagaaagg    4800 aagggaagaa agcgaaagga gcgggcgcta gggcgctggc aagtgtagcg gtcacgctgc    4860
gcgtaaccac cacacccgcc gcgcttaatg cgccgctaca gggcgcgtaa aaggatctag    4920
gtgaagatcc ttttttgataa tctcatgacc aaaatccctt aacgtgagtt ttcgttccac    4980
tgagcgtcag accccgtaga aagatcaaa ggatcttctt gagatccttt ttttctgcgc    5040
gtaatctgct gcttgcaaac aaaaaaacca ccgctaccag cggtggtttg tttgccggat    5100
caagagctac caactctttt tccgaaggta actggcttca gcagagcgca gataccaaat    5160
```

```
actgtccttc tagtgtagcc gtagttaggc caccacttca agaactctgt agcaccgcct   5220
acatacctcg ctctgctaat cctgttacca gtggctgctg ccagtggcga taagtcgtgt   5280
cttaccgggt tggactcaag acgatagtta ccggataagg cgcagcggtc gggctgaacg   5340
gggggttcgt gcacacagcc cagcttggag cgaacgacct acaccgaact gagataccta   5400
cagcgtgagc tatgagaaag cgccacgctt cccgaaggga gaaaggcgga caggtatccg   5460
gtaagcggca gggtcggaac aggagagcgc acgagggagc ttccagggg aaacgcctgg    5520 tatctttata gtcctgtcgg gtttcgccac ctctgacttg agcgtcgatt tttgtgatgc   5580
tcgtcagggg ggcggagcct atggaaaaac gccagcaacg cggccttttt acggttcctg   5640
gccttttgct ggccttttgc tcacatgttc tttcctgcgt tatcccctga ttctgtggat   5700
aaccgtatta ccgcctttga gtgagctgat accgctcgcc gcagccgaac gaccgagcgc   5760
agcgagtcag tgagcgagga agcggaagag cgcctgatgc ggtattttct ccttacgcat   5820
ctgtgcggta tttcacaccg catatatggt gcactctcag tacaatctgc tctgatgccg   5880
catagttaag ccagtataca ctccgctatc gctacgtgac tgggtcatgg ctgcgccccg   5940 acaccgcca acaccgctg acgcgccctg acgggcttgt ctgctcccgg catccgctta    6000
cagacaagct gtgaccgtct ccgggagctg catgtgtcag aggttttcac cgtcatcacc   6060
gaaacgcgcg aggcagctgc ggtaaagctc atcagcgtgg tcgtgcagcg attcacagat   6120
gtctgcctgt tcatccgcgt ccagctcgtt gagtttctcc agaagcgtta atgtctggct   6180
tctgataaag cgggccatgt taagggcggt ttttcctgt ttggtcactg atgcctccgt    6240
gtaaggggga tttctgttca tgggggtaat gataccgatg aaacgagaga ggatgctcac   6300
gatacgggtt actgatgatg aacatgcccg gttactggaa cgttgtgagg gtaaacaact   6360
ggcggtatgg atgcggcggg accagagaaa aatcactcag ggtcaatgcc agcgcttcgt   6420
taatacagat gtaggtgttc cacagggtag ccagcagcat cctgcgatgc agatccggaa   6480
cataatggtg cagggcgctg acttccgcgt ttccagactt tacgaaacac ggaaaccgaa   6540
gaccattcat gttgttgctc aggtcgcaga cgttttgcag cagcagtcgc ttcacgttcg   6600
ctcgcgtatc ggtgattcat tctgctaacc agtaaggcaa ccccgccagc ctagccgggt   6660
cctcaacgac aggagcacga tcatgcgcac ccgtggccag gacccaacgc tgcccgaaat   6720
t                                                                  6721
```

<210> SEQ ID NO 2
<211> LENGTH: 2803
<212> TYPE: DNA
<213> ORGANISM: Artificial
<220> FEATURE:
<223> OTHER INFORMATION: Plasmid pWKK-500.

<400> SEQUENCE: 2

```
tagcatatga aaataaaaac aggtgcacgc atcctcgcat tatccgcatt aacgacgatg     60
atgttttccg cctcggctct cgccaaaatc gaagaaggta aactggtaat ctggattaac    120
ggcgataaag ctataacgg tctcgctgaa gtcggtaaga aattcgagaa agataccgga     180
attaaagtca ccgttgagca tccggataaa ctggaagaga aattcccaca ggttgcggca    240
actggcgatg gccctgacat tatccttctg gcacacgacc gctttggtgg ctacgctcaa    300
tctggcctgt tggctgaaat caccccggac aaagcgttcc aggacaagct gtatccgttt    360
acctgggatg ccgtacgtta caacggcaag ctgattgctt acccgatcgc tgttgaagcg    420
ttatcgctga tttataacaa agatctgctg ccgaacccgc caaaaacctg ggaagagatc    480
```

-continued

```
ccggcgctgg ataaagaact gaaagcgaaa ggtaagagcg cgctgatgtt caacctgcaa    540
gaaccgtact tcacctggcc gctgattgct gctgacgggg ttatgcgtt caagtatgaa     600
aacggcaagt acgacattaa agacgtgggc gtggataacg ctggcgcgaa agcgggtctg    660
accttcctgg ttgacctgat taaaaacaaa cacatgaatg cagacaccga ttactccatc    720
gcagaagctg cctttaataa aggcgaaaca gcgatgacca tcaacggccc gtgggcatgg    780
tccaacatcg acaccagcaa agtgaattat ggtgtaacgg tactgccgac cttcaagggt    840
caaccatcca aaccgttcgt tggcgtgctg agcgcaggta ttaacgccgc cagtccgaac    900
aaagagctgg caaaagagtt cctcgaaaac tatctgctga ctgatgaagg tctggaagcg    960
gttaataaag acaaaccgct gggtgccgta gcgctgaagt cttacgagga agagttggcg   1020
aaagatccac gtattgccgc cactatggaa aacgcccaga aaggtgaaat catgccgaac   1080
atcccgcaga tgtccgcttt ctggtatgcc gtgcgtactg cggtgatcaa cgccgccagc   1140
ggtcgtcaga ctgtcgatga agccctgaaa gacgcgcaga ctaattcgag ctccgtacgt   1200
atgggcatcg agggacgtgg cgctcgagca tcatacacaa gcttaataca ctccttaatt   1260
gaagaatcgc aaaaccagca agaaaagaat gaacaagaac ttttggaact tgataaatgg   1320
gctagcttgt ggaactggtt taacaccggt gcgcatgcct cgactccaga accagacccg   1380
ggcgggcaat tccccaaaca atacccaatt ataaactta ccacagcggg tgccactgtg    1440
caaagctaca caaactttat cagagctgtt cgcggtcgtt taacaactgg agctgatgtg   1500
agacatgaaa taccagtgtt gccaaacaga gttggtttgc ctataaacca acggtttatt   1560
ttagttgacc tctcaaatca tgcagagctt tctgttacat tagcgctgga tgtcaccaat   1620
gcatatgtgt taggctaccg tgctggaaat agcgcatatt tctttcatcc tgacaatcag   1680
gaagatgcag aagcaatcac tcatcttttc actgatgttc aaaatcgata tacattcgcc   1740
tttggtggta attatgatag acttgaacaa cttgctggta atctgagaga aaatatcgag   1800
ttgggaaatg gtccactaga ggaggctatc tcagcgcttt attattacag tactggtggc   1860
actcagcttc caactctggc tcgttccttt ataatttgca tccaaatgat tcagaagca    1920
gcaagattcc aatatattga gggagaaatg cgcacgagaa ttaggtacaa ccggagatct   1980
gcaccagatc ctagcgtaat tacacttgag aatagttggg ggagactttc cactgcaatt   2040
caagagtcta accaaggagc ctttgctagt ccaattcaac tgcaaagacg taatggttcc   2100
aaattcagtg tgtacgatgt gagtatatta atccctatca tagctctcat ggtgtacaga   2160
tgcgcacctc caccatcgtc acaattgggt gtttctcaaa attatcccat cgttcaaaat   2220
gctgcagatg tttgtatgga tcctgagcca ctagtgcgga tcccggttag tatcctcata   2280
cccataatcg ccttagcctc agcaccacct ccgccatacc ttaaggacga actctaggga   2340
tccatggtac cgttcatcga gggcaggact tcagtttcca gtcggcctca gggttcatcg   2400
cctcttacgg aagttgttct agagagcttg gcactggccg tcgttttaca acgtcgtgac   2460
tgggaaaacc ctggcgttac ccaacttaat cgccttgcag cacatccccc tttcgccagc   2520
tggcgtaata gcgaagaggc ccgcaccgat cgcccttccc aacagttgcg cagcctgaat   2580
ggtgaattcc atcatcatca tcatcattga cctagagagc ttggcactgg ccgtcgtttt   2640
acaacgtcgt gactgggaaa accctggcgt tacccaactt aatcgccttg cagcacatcc   2700
cccttttcgcc agctggcgta atagcgaaga ggccgcacc gatcgccctt cccaacagtt   2760
gcgcagcctg aatggtgaat tccatcatca tcatcatcat tga                     2803
```

-continued

```
<210> SEQ ID NO 3
<211> LENGTH: 4
<212> TYPE: PRT
<213> ORGANISM: Artificial
<220> FEATURE:
<223> OTHER INFORMATION: Recognition sequence for Factor Xa protease.

<400> SEQUENCE: 3

Ile Glu Gly Arg
1

<210> SEQ ID NO 4
<211> LENGTH: 5
<212> TYPE: PRT
<213> ORGANISM: Human immunodeficiency virus

<400> SEQUENCE: 4

Gly Ala Arg Ala Ser
1               5

<210> SEQ ID NO 5
<211> LENGTH: 36
<212> TYPE: PRT
<213> ORGANISM: Human immunodeficiency virus

<400> SEQUENCE: 5

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 6
<211> LENGTH: 16
<212> TYPE: PRT
<213> ORGANISM: Artificial
<220> FEATURE:
<223> OTHER INFORMATION: Flexible linker.

<400> SEQUENCE: 6

Asn Thr Gly Ala His Ala Ser Thr Pro Glu Pro Asp Pro Gly Gly Gln
1               5                   10                  15

<210> SEQ ID NO 7
<211> LENGTH: 266
<212> TYPE: PRT
<213> ORGANISM: Ricinus communis

<400> SEQUENCE: 7

Phe Pro Lys Gln Tyr Pro Ile Ile Asn Phe Thr Thr Ala Gly Ala Thr
1               5                   10                  15

Val Gln Ser Tyr Thr Asn Phe Ile Arg Ala Val Arg Gly Arg Leu Thr
            20                  25                  30

Thr Gly Ala Asp Val Arg His Glu Ile Pro Val Leu Pro Asn Arg Val
        35                  40                  45

Gly Leu Pro Ile Asn Gln Arg Phe Ile Leu Val Asp Leu Ser Asn His
    50                  55                  60

Ala Glu Leu Ser Val Thr Leu Ala Leu Asp Val Thr Asn Ala Tyr Val
65                  70                  75                  80

Val Gly Tyr Arg Ala Gly Asn Ser Ala Tyr Phe Phe His Pro Asp Asn
                85                  90                  95
```

-continued

```
Gln Glu Asp Ala Glu Ala Ile Thr His Leu Phe Thr Asp Val Gln Asn
                100                 105                 110
Arg Tyr Thr Phe Ala Phe Gly Gly Asn Tyr Asp Arg Leu Glu Gln Leu
            115                 120                 125
Ala Gly Asn Leu Arg Glu Asn Ile Glu Leu Gly Asn Gly Pro Leu Glu
        130                 135                 140
Glu Ala Ile Ser Ala Leu Tyr Tyr Tyr Ser Thr Gly Gly Thr Gln Leu
145                 150                 155                 160
Pro Thr Leu Ala Arg Ser Phe Ile Ile Cys Ile Gln Met Ile Ser Glu
                165                 170                 175
Ala Ala Arg Phe Gln Tyr Ile Glu Gly Glu Met Arg Thr Arg Ile Arg
            180                 185                 190
Tyr Asn Arg Arg Ser Ala Pro Asp Pro Ser Val Ile Thr Leu Glu Asn
        195                 200                 205
Ser Trp Gly Arg Leu Ser Thr Ala Ile Gln Glu Ser Asn Gln Gly Ala
    210                 215                 220
Phe Ala Ser Pro Ile Gln Leu Gln Arg Arg Asn Gly Ser Lys Phe Ser
225                 230                 235                 240
Val Tyr Asp Val Ser Ile Leu Ile Pro Ile Ile Ala Leu Met Val Tyr
                245                 250                 255
Arg Cys Ala Pro Pro Ser Ser Gln Leu
            260                 265

<210> SEQ ID NO 8
<211> LENGTH: 10
<212> TYPE: PRT
<213> ORGANISM: Human immunodeficiency virus

<400> SEQUENCE: 8

Val Ser Gln Asn Tyr Pro Ile Val Gln Asn
1               5                   10

<210> SEQ ID NO 9
<211> LENGTH: 14
<212> TYPE: PRT
<213> ORGANISM: Ricinus communis

<400> SEQUENCE: 9

Ala Asp Val Cys Met Asp Pro Glu Pro Leu Val Arg Ile Pro
1               5                   10

<210> SEQ ID NO 10
<211> LENGTH: 13
<212> TYPE: PRT
<213> ORGANISM: Ricinus communis

<400> SEQUENCE: 10

Val Ser Ile Leu Ile Pro Ile Ile Ala Leu Ala Ser Ala
1               5                   10

<210> SEQ ID NO 11
<211> LENGTH: 5
<212> TYPE: PRT
<213> ORGANISM: Rous sarcoma virus

<400> SEQUENCE: 11

Pro Pro Pro Pro Tyr
1               5
```

```
<210> SEQ ID NO 12
<211> LENGTH: 4
<212> TYPE: PRT
<213> ORGANISM: Homo sapiens

<400> SEQUENCE: 12

Lys Asp Glu Leu
1

<210> SEQ ID NO 13
<211> LENGTH: 5
<212> TYPE: PRT
<213> ORGANISM: Artificial
<220> FEATURE:
<223> OTHER INFORMATION: Enterokinase recognition site.

<400> SEQUENCE: 13

Asp Asp Asp Asp Lys
1               5

<210> SEQ ID NO 14
<211> LENGTH: 21
<212> TYPE: PRT
<213> ORGANISM: Bufo bufo gargarizans

<400> SEQUENCE: 14

Arg Ser Ser Arg Ala Gly Leu Gln Phe Pro Val Gly Leu Arg Val His
1               5                  10                  15

Arg Leu Leu Arg Lys
            20

<210> SEQ ID NO 15
<211> LENGTH: 56
<212> TYPE: DNA
<213> ORGANISM: Artificial
<220> FEATURE:
<223> OTHER INFORMATION: BZ primer for constructing pWKK-501.

<400> SEQUENCE: 15
accctaggtc aatgatgatg atgatgatgg aattcaccat tcaggctgcg caactg        56

<210> SEQ ID NO 16
<211> LENGTH: 62
<212> TYPE: DNA
<213> ORGANISM: Artificial
<220> FEATURE:
<223> OTHER INFORMATION: LT-1 primer for constructing pWKK-501.

<400> SEQUENCE: 16
gggcttaagg acgaactcta gggatccatg gtaccgttca tcgagggcag gacttcagtt    60
tc                                                                  62

<210> SEQ ID NO 17
<211> LENGTH: 29
<212> TYPE: DNA
<213> ORGANISM: Artificial
<220> FEATURE:
<223> OTHER INFORMATION: Oligonucleotide for constructing pWKK-505.
<220> FEATURE:
<221> NAME/KEY: misc_feature
<222> LOCATION: (14)..(23)
<223> OTHER INFORMATION: n is a, c, g, or t

<400> SEQUENCE: 17
cggaagtagg cctnnnnnnn nnntctaga                                     29
```

<210> SEQ ID NO 18
<211> LENGTH: 41
<212> TYPE: DNA
<213> ORGANISM: Artificial
<220> FEATURE:
<223> OTHER INFORMATION: Upper oligonucleotide for cassette for
    alternative HIV protease cleavable linker.

<400> SEQUENCE: 18
aattgtctgc tactattatg atgcaacgag gcaatggtgc a                 41

<210> SEQ ID NO 19
<211> LENGTH: 33
<212> TYPE: DNA
<213> ORGANISM: Artificial
<220> FEATURE:
<223> OTHER INFORMATION: Lower oligonucleotide for cassette for
    alternative HIV protease cleavable linker.

<400> SEQUENCE: 19
ccattgcctc gttgcatcat aatagtagca gac                          33

<210> SEQ ID NO 20
<211> LENGTH: 2869
<212> TYPE: DNA
<213> ORGANISM: Artificial
<220> FEATURE:
<223> OTHER INFORMATION: Coding region of pWKK-700.

<400> SEQUENCE: 20
tagcatatga aaataaaaac aggtgcacgc atcctcgcat tatccgcatt aacgacgatg     60
atgttttccg cctcggctct cgccaaaatc gaagaaggta aactggtaat ctggattaac    120
ggcgataaag ctataacgg tctcgctgaa gtcggtaaga aattcgagaa agataccgga    180
attaaagtca ccgttgagca tccggataaa ctggaagaga aattcccaca ggttgcggca    240
actggcgatg ccctgacat tatcttctgg gcacacgacc gctttggtgg ctacgctcaa    300
tctggcctgt tggctgaaat caccccggac aaagcgttcc aggacaagct gtatccgttt    360
acctgggatg ccgtacgtta caacggcaag ctgattgctt acccgatcgc tgttgaagcg    420
ttatcgctga tttataacaa agatctgctg ccgaacccgc caaaaacctg gaagagatc    480 ccggcgctgg ataaagaact gaaagcgaaa ggtaagagcg cgctgatgtt caacctgcaa    540
gaaccgtact tcacctggcc gctgattgct gctgacgggg gttatgcgtt caagtatgaa    600
aacggcaagt acgacattaa agacgtgggc gtggataacg ctggcgcgaa agcgggtctg    660
accttcctgg ttgacctgat taaaaacaaa cacatgaatg cagacaccga ttactccatc    720
gcagaagctg cctttaataa aggcgaaaca gcgatgacca tcaacggccc gtgggcatgg    780
tccaacatcg acaccagcaa agtgaattat ggtgtaacgg tactgccgac cttcaagggt    840
caaccatcca aaccgttcgt tggcgtgctg agcgcaggta ttaacgccgc cagtccgaac    900
aaagagctgg caaaagagtt cctcgaaaac tatctgctga ctgatgaagg tctggaagcg    960
gttaataaag acaaaccgct gggtgccgta gcgctgaagt cttacgagga agagttggcg   1020
aaagatccac gtattgccgc cactatggaa aacgcccaga aggtgaaat catgccgaac    1080 atcccgcaga tgtccgcttt ctggtatgcc gtgcgtactg cggtgatcaa cgccgccagc    1140
ggtcgtcaga ctgtcgatga agccctgaaa gacgcgcaga ctaattcgag ctccgtacgt    1200
atgggcattg agggtcgcga catgagtcct tactcgagtg acaccacacc atgctgcttc    1260
gcctacattg cccgcccact gccacgtgcc cacatcaagg agtacttcta caccagcggc    1320

```
aaatgttcga acccagcagt cgtattcgtc actcgtaaga atcgccaagt gtgtgccaat    1380
cctgagaaga aatgggttcg tgagtacatc aacagtttgg agatgagtac cggtgcgcat    1440
gcctcgactc cagaaccaga cccgggcggg caattcccca acaataccc aattataaac     1500 tttaccacag cgggtgccac tgtgcaaagc tacacaaact ttatcagagc tgttcgcggt    1560
cgtttaacaa ctggagctga tgtgagacat gaaataccag tgttgccaaa cagagttggt    1620
ttgcctataa accaacggtt tattttagtt gacctctcaa atcatgcaga gctttctgtt    1680
acattagcgc tggatgtcac caatgcatat gtggtaggct accgtgctgg aaatagcgca    1740
tatttctttc atcctgacaa tcaggaagat gcagaagcaa tcactcatct tttcactgat    1800
gttcaaaatc gatatacatt cgcctttggt ggtaattatg atagacttga caacttgct     1860 ggtaatctga gagaaaatat cgagttggga atggtccac tagaggaggc tatctcagcg     1920
ctttattatt acagtactgg tggcactcag cttccaactc tggctcgttc ctttataatt    1980
tgcatccaaa tgatttcaga agcagcaaga ttccaatata ttgagggaga aatgcgcacg    2040
agaattaggt acaaccggag atctgcacca gatcctagcg taattacact tgagaatagt    2100
tgggggagac tttccactgc aattcaagag tctaaccaag gagcctttgc tagtccaatt    2160
caactgcaaa gacgtaatgg ttccaaattc agtgtgtacg atgtgagtat attaatccct    2220
atcatagctc tcatggtgta cagatgcgca cctccaccat cgtcacaatt gggtgtttct    2280
caaaattatc ccatcgttca aaatgctgca gatgtttgta tggatcctga gccactagtg    2340
cggatcccgg ttagtatcct catacccata atcgccttag cctcagcacc acctccgcca    2400
taccttaagg acgaactcta gggatccatg gtaccgttca tcgagggcag gacttcagtt    2460
tccagtcggc ctcagggttc atcgcctctt acggaagttg ttctagagag cttggcactg    2520
gccgtcgttt tacaacgtcg tgactgggaa accctggcg ttacccaact taatcgcctt     2580
gcagcacatc cccctttcgc cagctggcgt aatagcgaag aggcccgcac cgatcgccct    2640
tcccaacagt tgcgcagcct gaatggtgaa ttccatcatc atcatcatca ttgacctaga    2700
gagcttggca ctgccgtcg ttttacaacg tcgtgactgg gaaaaccctg gcgttaccca    2760
acttaatcgc cttgcagcac atccccctt cgccagctgg cgtaatagcg aagaggcccg    2820
caccgatcgc ccttcccaac agttgcgcag cctgaatggc gaatggcag                2869
```

<210> SEQ ID NO 21
<211> LENGTH: 75
<212> TYPE: DNA
<213> ORGANISM: Artificial
<220> FEATURE:
<223> OTHER INFORMATION: Oligonucleotide OC-1 for making pWKK-700.

<400> SEQUENCE: 21

```
agtgacacca caccatgctg cttcgcctac attgcccgcc cactgccacg tgcccacatc    60
aaggagtact tctac                                                     75
```

<210> SEQ ID NO 22
<211> LENGTH: 72
<212> TYPE: DNA
<213> ORGANISM: Artificial
<220> FEATURE:
<223> OTHER INFORMATION: Oligonucleotide OC-2 for making pWKK-700.

<400> SEQUENCE: 22

```
accagcggca aatgttcgaa cccagcagtc gtattcgtca ctcgtaagaa tcgccaagtg    60
```

-continued

<210> SEQ ID NO 23
<211> LENGTH: 46
<212> TYPE: DNA
<213> ORGANISM: Artificial
<220> FEATURE:
<223> OTHER INFORMATION: Oligonucleotide OC-5 for making pWKK-700.

<400> SEQUENCE: 23
ggttcgaaca tttgccgctg gtgtagaagt actccttgat gtgggc          46

<210> SEQ ID NO 24
<211> LENGTH: 73
<212> TYPE: DNA
<213> ORGANISM: Artificial
<220> FEATURE:
<223> OTHER INFORMATION: Oligonucleotide OC-3 for making pWKK-700.

<400> SEQUENCE: 24
ggcgagctcc gtacgtatgg gcattgaggg tcgcgacatg agtccttact cgagtgacac    60
cacaccatgc tgc                                                      73

<210> SEQ ID NO 25
<211> LENGTH: 75
<212> TYPE: DNA
<213> ORGANISM: Artificial
<220> FEATURE:
<223> OTHER INFORMATION: Oligonucleotide OC-4 for making pWKK-700.

<400> SEQUENCE: 25
cgcaccggta ctcatctcca aactgttgat gtactcacga acccatttct tctcaggatt    60
ggcacacact tggcg                                                    75

<210> SEQ ID NO 26
<211> LENGTH: 2878
<212> TYPE: DNA
<213> ORGANISM: Artificial
<220> FEATURE:
<223> OTHER INFORMATION: pWKK-800

<400> SEQUENCE: 26
tagcatatga aaataaaaac aggtgcacgc atcctcgcat tatccgcatt aacgacgatg    60
atgttttccg cctcggctct cgccaaaatc gaagaaggta aactggtaat ctggattaac   120
ggcgataaag gctataacgg tctcgctgaa gtcggtaaga aattcgagaa agataccgga   180
attaaagtca ccgttgagca tccggataaa ctggaagaga attcccaca ggttgcggca    240 actggcgatg gccctgacat tatcttctgg gcacacgacc gctttggtgg ctacgctcaa   300
tctggcctgt tggctgaaat caccccggac aaagcgttcc aggacaagct gtatccgttt   360
acctgggatg ccgtacgtta caacggcaag ctgattgctt acccgatcgc tgttgaagcg   420
ttatcgctga tttataacaa agatctgctg ccgaacccgc caaaaacctg gaagagatc    480 ccggcgctgg ataagaact gaaagcgaaa ggtaagagcg cgctgatgtt caacctgcaa   540
gaaccgtact tcacctggcc gctgattgct gctgacgggg ttatgcgtt caagtatgaa   600 aacggcaagt acgacattaa agacgtgggc gtggataacg ctggcgcgaa agcgggtctg    660
accttcctgg ttgacctgat taaaaacaaa cacatgaatg cagacaccga ttactccatc    720
gcagaagctg cctttaataa aggcgaaaca gcgatgacca tcaacggccc gtgggcatgg    780
tccaacatcg acaccagcaa agtgaattat ggtgtaacgg tactgccgac cttcaagggt   840

-continued

```
caaccatcca aaccgttcgt tggcgtgctg agcgcaggta ttaacgccgc cagtccgaac      900
aaagagctgg caaaagagtt cctcgaaaac tatctgctga ctgatgaagg tctggaagcg      960
gttaataaag acaaaccgct gggtgccgta gcgctgaagt cttacgagga agagttggcg     1020
aaagatccac gtattgccgc cactatggaa aacgcccaga aggtgaaat catgccgaac      1080
atcccgcaga tgtccgcttt ctggtatgcc gtgcgtactg cggtgatcaa cgccgccagc     1140
ggtcgtcaga ctgtcgatga agccctgaaa gacgcgcaga ctaattcgag ctccgtacgt     1200
atgggaattg agggtcgcaa gccagtcagt ttgagctacc gttgcccatg ccgtttcttc     1260
gaaagccatg ttgcacgtgc aacgtcaag catctcaaaa tcctcaatac tccaaactgt      1320
gcattacaaa ttgtggcgcg cctgaagaac aacaaccgtc aagtgtgcat cgaccctaag     1380
cttaaatgga ttcaagagta cctggagaag gccttaaata agcgtttcaa gatgacgtcg     1440
gtcgggcatg cctcgactcc agaaccagac cggggcgggc aattcccaa acaatacccca     1500
attataaact ttaccacagc gggtgccact gtgcaaagct acacaaactt tatcagagct     1560
gttcgcggtc gtttaacaac tggagctgat gtgagacatg aaataccagt gttgccaaac     1620
agagttggtt tgcctataaa ccaacggttt attttagttg acctctcaaa tcatgcagag     1680
ctttctgtta cattagcgct ggatgtcacc aatgcatatg tggtaggcta ccgtgctgga     1740
aatagcgcat atttctttca tcctgacaat caggaagatg cagaagcaat cactcatctt     1800
ttcactgatg ttcaaaatcg atatacattc gcctttggtg gtaattatga tagacttgaa     1860
caacttgctg gtaatctgag agaaaatatc gagttgggaa atggtccact agaggaggct     1920
atctcagcgc tttattatta cagtactggt ggcactcagc ttccaactct ggctcgttcc     1980
tttataattt gcatccaaat gatttcagaa gcagcaagat tccaatatat tgagggagaa     2040
atgcgcacga gaattaggta caaccggaga tctgcaccag atcctagcgt aattacactt     2100
gagaatagtt gggggagact ttccactgca attcaagagt ctaaccaagg agcctttgct     2160
agtccaattc aactgcaaag acgtaatggt tccaaattca gtgtgtacga tgtgagtata     2220
ttaatcccta tcatagctct catggtgtac agatgcgcac ctccaccatc gtcacaattg     2280
ggtgtttctc aaaattatcc catcgttcaa aatgctgcag atgtttgtat ggatcctgag     2340
ccactagtgc ggatcccggt tagtatcctc ataccccataa tcgccttagc ctcagcacca     2400
cctccgccat accttaagga cgaactctag ggatccatgg taccgttcat cgagggcagg     2460
acttcagttt ccagtcggcc tcagggttca tcgcctctta cggaagttgt tctagagagc     2520
ttggcactgg ccgtcgtttt acaacgtcgt gactgggaaa accctggcgt tacccaactt     2580
aatcgccttg cagcacatcc ccctttcgcc agctggcgta atagcgaaga ggcccgcacc     2640
gatcgccctt cccaacagtt gcgcagcctg aatggtgaat ccatcatca tcatcatcat     2700
tgacctagag agcttggcac tggccgtcgt tttacaacgt cgtgactggg aaaaccctgg     2760
cgttacccaa cttaatcgcc ttgcagcaca tccccctttc gccagctggc gtaatagcga     2820
agaggcccgc accgatcgcc cttcccaaca gttgcgcagc ctgaatggcg aatggcag      2878
```

<210> SEQ ID NO 27
<211> LENGTH: 75
<212> TYPE: DNA
<213> ORGANISM: Artificial
<220> FEATURE:
<223> OTHER INFORMATION: Oligonucleotide AB-2 primer for making pWKK-800.

<400> SEQUENCE: 27

```
cttctccagg tactcttgaa tccatttaag cttagggtcg atgcacactt gacggttgtt    60
gttcttcagg cgcgc                                                     75
```

<210> SEQ ID NO 28
<211> LENGTH: 75
<212> TYPE: DNA
<213> ORGANISM: Artificial
<220> FEATURE:
<223> OTHER INFORMATION: Oligonucleotide AB-3 primer for making
      pWKK-800.

<400> SEQUENCE: 28

```
acgtcaagca tctcaaaatc ctcaatactc caaactgtgc attacaaatt gtggcgcgcc    60
tgaagaacaa caacc                                                     75
```

<210> SEQ ID NO 29
<211> LENGTH: 73
<212> TYPE: DNA
<213> ORGANISM: Artificial
<220> FEATURE:
<223> OTHER INFORMATION: Oligonucleotide AB-5 primer for making
      pWKK-800.

<400> SEQUENCE: 29

```
gagctaccgt tgcccatgcc gtttcttcga aagccatgtt gcacgtgcca acgtcaagca    60
tctcaaaatc ctc                                                       73
```

<210> SEQ ID NO 30
<211> LENGTH: 69
<212> TYPE: DNA
<213> ORGANISM: Artificial
<220> FEATURE:
<223> OTHER INFORMATION: Oligonucleotide AB-1 primer for making
      pWKK-800.

<400> SEQUENCE: 30

```
caccagcatg cccgaccgac gtcatcttga aacgcttatt taaggccttc tccaggtact    60
cttgaatcc                                                            69
```

<210> SEQ ID NO 31
<211> LENGTH: 69
<212> TYPE: DNA
<213> ORGANISM: Artificial
<220> FEATURE:
<223> OTHER INFORMATION: Oligonucleotide AB-4 primer for making
      pWKK-800.

<400> SEQUENCE: 31

```
ggcgagctcc gtacgtatgg gaattgaggg tcgcaagcca gtcagtttga gctaccgttg    60
cccatgccg                                                            69
```

<210> SEQ ID NO 32
<211> LENGTH: 13
<212> TYPE: PRT
<213> ORGANISM: Artificial
<220> FEATURE:
<223> OTHER INFORMATION: Lethal factor cleavable sequence.

<400> SEQUENCE: 32

Pro Lys Lys Lys Pro Thr Pro Ile Gln Leu Asn Pro Ala
1               5                   10

<210> SEQ ID NO 33
<211> LENGTH: 47
<212> TYPE: DNA
<213> ORGANISM: Artificial
<220> FEATURE:
<223> OTHER INFORMATION: pWKK-900 upper oligonucleotide in cassette
      encoding lethal factor cleavable peptide sequence.

<400> SEQUENCE: 33
aattgcctaa gaagaaacct actcctatcc aggccaatcc ggctgca 47

<210> SEQ ID NO 34
<211> LENGTH: 39
<212> TYPE: DNA
<213> ORGANISM: Artificial
<220> FEATURE:
<223> OTHER INFORMATION: pWKK-900 lower oligonucleotide in cassette encoding lethal factor cleavable peptide sequence.

<400> SEQUENCE: 34
gccggattgg cctggatagg agtaggtttc ttcttaggc 39

<210> SEQ ID NO 35
<211> LENGTH: 2788
<212> TYPE: DNA
<213> ORGANISM: Artificial
<220> FEATURE:
<223> OTHER INFORMATION: pWKK-21

<400> SEQUENCE: 35
tagcatatga aaataaaaac aggtgcacgc atcctcgcat tatccgcatt aacgacgatg 60
atgttttccg cctcggctct cgccaaaatc gaagaaggta aactggtaat ctggattaac 120
ggcgataaag gctataacgg tctcgctgaa gtcggtaaga aattcgagaa agataccgga 180
attaaagtca ccgttgagca tccggataaa ctggaagaga aattcccaca ggttgcggca 240
actggcgatg gccctgacat tatcttctgg gcacacgacc gctttggtgg ctacgctcaa 300
tctggcctgt tggctgaaat caccccggac aaagcgttcc aggacaagct gtatccgttt 360
acctgggatg ccgtacgtta caacggcaag ctgattgctt acccgatcgc tgttgaagcg 420
ttatcgctga tttataacaa agatctgctg ccgaacccgc caaaaacctg ggaagagatc 480
ccggcgctgg ataaagaact gaaagcgaaa ggtaagagcg cgctgatgtt caacctgcaa 540
gaaccgtact tcacctggcc gctgattgct gctgacgggg gttatgcgtt caagtatgaa 600
aacggcaagt acgacattaa agacgtgggc gtggataacg ctggcgcgaa agcgggtctg 660
accttcctgg ttgacctgat taaaaacaaa cacatgaatg cagacaccga ttactccatc 720
gcagaagctg cctttaataa aggcgaaaca gcgatgacca tcaacggccc gtgggcatgg 780
tccaacatcg acaccagcaa agtgaattat ggtgtaacgg tactgccgac cttcaagggt 840
caaccatcca aaccgttcgt tggcgtgctg agcgcaggta ttaacgccgc cagtccgaac 900
aaagagctgg caaaagagtt cctcgaaaac tatctgctga ctgatgaagg tctggaagcg 960
gttaataaag acaaaccgct gggtgccgta gcgctgaagt cttacgagga agagttggcg 1020
aaagatccac gtattgccgc cactatggaa aacgcccaga aaggtgaaat catgccgaac 1080
atcccgcaga tgtccgcttt ctggtatgcc gtgcgtactg cggtgatcaa cgccgccagc 1140
ggtcgtcaga ctgtcgatga agccctgaaa gacgcgcaga ctaattcgag ctctatcgag 1200
ggtcgactct ctcgaggtgc tcgtgcaagc accggtgcgc atgcctcgac tccagaacca 1260
gacccgggcg ggcaattccc caaacaatac ccaattataa actttaccac agcgggtgcc 1320

```
actgtgcaaa gctacacaaa ctttatcaga gctgttcgcg gtcgtttaac aactggagct    1380
gatgtgagac atgaaatacc agtgttgcca acagagttg gtttgcctat aaaccaacgg     1440
tttattttag ttgacctctc aaatcatgca gagctttctg ttacattagc gctggatgtc    1500
accaatgcat atgtggtagg ctaccgtgct ggaaatagcg catatttctt tcatcctgac    1560
aatcaggaag atgcagaagc aatcactcat cttttcactg atgttcaaaa tcgatataca    1620
ttcgcctttg gtggtaatta tgatagactt gaacaacttg ctggtaatct gagagaaaat    1680
atcgagttgg gaaatggtcc actagaggag gctatctcag cgctttatta ttacagtact    1740
ggtggcactc agcttccaac tctggctcgt tcctttataa tttgcatcca aatgatttca    1800
gaagcagcaa gattccaata tattgaggga gaaatgcgca cgagaattag gtacaaccgg    1860
agatctgcac cagatcctag cgtaattaca cttgagaata gttgggggag actttccact    1920
gcaattcaag agtctaacca aggagccttt gctagtccaa ttcaactgca aagacgtaat    1980
ggttccaaat tcagtgtgta cgatgtgagt atattaatcc ctatcatagc tctcatggtg    2040
tacagatgcg cacctccacc atcgtcacaa ttgggtgttt ctcaaaatta tcccatcgtt    2100
caaaatgctg cagatgtttg tatggatcct gagcccatag tgcgtatcgt aggtcgaaat    2160
ggtctatgtg ttgatgttag ggatggaaga ttccacaacg gaaacgcaat acagttgtgg    2220
ccatgcaagt ctaatacaga tgcaaatcag ctctggacat tgaaaagaga caatactatt    2280
cgatctaatg gaaagtgttt aactacttac gggtacagtc cgggagtcta tgtgatgatc    2340
tatgattgca atactgctgc aactgatgcc acccgctgga tgttcaagaa tgatggaacc    2400
attttaaatt tgtatagtgg gttggtgtta gatgtgaggg catcggatcc gagccttaaa    2460
caaatcattc tttaccctct ccatggtgac ccaaaccaaa tatggttacc ccttaaggag    2520
ctagccatcc tcatacccat aatcgcctta gcctcagcac cacctccgcc ataccttaag    2580
gacgaactct agagagcttg gcactggccg tcgttttaca acgtcgtgac tgggaaaacc    2640
ctggcgttac ccaacttaat cgccttgcag cacatccccc tttcgccagc tggcgtaata    2700
gcgaagaggc ccgcaccgat cgcccttccc aacagttgcg cagcctgaat ggcgaatggc    2760
agcttggctg ttttggcgga tgagataa                                       2788

<210> SEQ ID NO 36
<211> LENGTH: 46
<212> TYPE: DNA
<213> ORGANISM: Artificial
<220> FEATURE:
<223> OTHER INFORMATION: Cassette encoding HIV protease-cleavable
      peptide linker.

<400> SEQUENCE: 36
caattgggtg tttctcaaaa ttatcccatc gttcaaaatg ctgcag            46

<210> SEQ ID NO 37
<211> LENGTH: 2805
<212> TYPE: DNA
<213> ORGANISM: Artificial
<220> FEATURE:
<223> OTHER INFORMATION: pWKK-15

<400> SEQUENCE: 37
tagcatatga aaataaaaac aggtgcacgc atcctcgcat tatccgcatt aacgacgatg    60
atgttttccg cctcggctct cgccaaaatc gaagaaggta aactggtaat ctggattaac    120
ggcgataaag gctataacgg tctcgctgaa gtcggtaaga aattcgagaa agataccgga    180
```

| | |
|---|---|
| attaaagtca ccgttgagca tccggataaa ctggaagaga aattcccaca ggttgcggca | 240 |
| actggcgatg gccctgacat tatcttctgg gcacacgacc gctttggtgg ctacgctcaa | 300 |
| tctggcctgt tggctgaaat caccccggac aaagcgttcc aggacaagct gtatccgttt | 360 |
| acctgggatg ccgtacgtta aacggcaagc tgattgctt acccgatcgc tgttgaagcg | 420 |
| ttatcgctga tttataacaa agatctgctg ccgaacccgc caaaaacctg gaagagatc | 480 |
| ccggcgctgg ataaagaact gaaagcgaaa ggtaagagcg cgctgatgtt caacctgcaa | 540 |
| gaaccgtact tcacctggcc gctgattgct gctgacgggg ttatgcgtt caagtatgaa | 600 |
| aacggcaagt acgacattaa agacgtgggc gtggataacg ctggcgcgaa agcgggtctg | 660 |
| accttcctgg ttgacctgat taaaaacaaa cacatgaatg cagacaccga ttactccatc | 720 |
| gcagaagctg cctttaataa aggcgaaaca gcgatgacca tcaacggccc gtgggcatgg | 780 |
| tccaacatcg acaccagcaa agtgaattat ggtgtaacgg tactgccgac cttcaagggt | 840 |
| caaccatcca aaccgttcgt tggcgtgctg agcgcaggta ttaacgccgc cagtccgaac | 900 |
| aaagagctgg caaaagagtt cctcgaaaac tatctgctga ctgatgaagg tctggaagcg | 960 |
| gttaataaag acaaaccgct gggtgccgta gcgctgaagt cttacgagga agagttggcg | 1020 |
| aaagatccac gtattgccgc cactatggaa aacgcccaga aggtgaaat catgccgaac | 1080 |
| atcccgcaga tgtccgcttt ctggtatgcc gtgcgtactg cggtgatcaa cgccgccagc | 1140 |
| ggtcgtcaga ctgtcgatga agccctgaaa gacgcgcaga ctaattcgag ctctaatatg | 1200 |
| ggaggaggca tcgagggacg tggcgctcga gcatcataca caagcttaat acactcctta | 1260 |
| attgaagaat cgcaaaacca gcaagaaaag aatgaacaag aacttttgga acttgataaa | 1320 |
| tgggctagct tgtggaactg gtttaacacc ggtgcgcatg cctcgactcc agaaccagac | 1380 |
| ccgggcgggc aattccccaa acaatacccca attataaact ttaccacagc gggtgccact | 1440 |
| gtgcaaagct acacaaactt tatcagagct gttcgcggtc gtttaacaac tggagctgat | 1500 |
| gtgagacatg aaataccagt gttgccaaac agagttggtt tgcctataaa ccaacggttt | 1560 |
| attttagttg acctctcaaa tcatgcagag ctttctgtta cattagcgct ggatgtcacc | 1620 |
| aatgcatatg tggtaggcta ccgtgctgga aatagcgcat atttctttca tcctgacaat | 1680 |
| caggaagatg cagaagcaat cactcatctt ttcactgatg ttcaaaatcg atatacattc | 1740 |
| gcctttggtg gtaattatga tagacttgaa caacttgctg gtaatctgag agaaaatatc | 1800 |
| gagttgggaa atggtccact agaggaggct atctcagcgc tttattatta cagtactggt | 1860 |
| ggcactcagc ttccaactct ggctcgttcc tttataattt gcatccaaat gatttcagaa | 1920 |
| gcagcaagat tccaatatat tgagggaaa atgcgcacga gaattaggta caaccggaga | 1980 |
| tctgcaccag atcctagcgt aattacactt gagaatagtt gggggagact ttccactgca | 2040 |
| attcaagagt ctaaccaagg agcctttgct agtccaattc aactgcaaag acgtaatggt | 2100 |
| tccaaattca gtgtgtacga tgtgagtata ttaatcccta tcatagctct catggtgtac | 2160 |
| agatgcgcac ctccaccatc gtcacaattg ggtgtttctc aaaattatcc catcgttcaa | 2220 |
| aatgctgcag atgtttgtat ggatcctgag cccatagtgc gtatcgtagg tcgaaatggt | 2280 |
| ctatgtgttg atgttagaga tggaagattc cacaacggaa acgcaataca gttgtggcca | 2340 |
| tgcaagtcta atacagatgc aaatcagctc tggacttttga aaagagacaa tactattcga | 2400 |
| tctaatggaa agtgtttaac tacttacggg tacagtccgg gagtctatgt gatgatctat | 2460 |
| gattgcaata ctgctgcaac tgatgccacc cgctggatgt tcaagaatga tggaaccatt | 2520 |
| ttaaatttgt atagtgggtt ggtgttagat gtgagggcat cggatccgag ccttaaacaa | 2580 |

```
atcattcttt accctctcca tggtgaccca aaccaaatat ggttacccct taaggagcta    2640
gccatcctca tacccataat cgccttagcc tcagcaccac ctccgccata ccttaaggac    2700
gaactctaga gagcttggca ctggccgtcg ttttacaacg tcgtgactgg gaaaaccctg    2760
gcgttaccca acttaatcgc cttgcagcac atccccctttt cgcca                   2805
```

<210> SEQ ID NO 38
<211> LENGTH: 12
<212> TYPE: PRT
<213> ORGANISM: Ricinus communis

<400> SEQUENCE: 38

Val Ser Ile Leu Ile Pro Ile Ile Ala Leu Met Val
1               5                   10

<210> SEQ ID NO 39
<211> LENGTH: 68
<212> TYPE: PRT
<213> ORGANISM: Homo sapiens

<400> SEQUENCE: 39

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 40
<211> LENGTH: 72
<212> TYPE: PRT
<213> ORGANISM: Homo sapiens

<400> SEQUENCE: 40

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 41
<211> LENGTH: 18
<212> TYPE: PRT
<213> ORGANISM: Homo sapiens

<400> SEQUENCE: 41

Lys Pro Val Ser Leu Ser Tyr Arg Cys Pro Cys Arg Phe Phe Glu Ser
1               5                   10                  15

His Val

```
<210> SEQ ID NO 42
<211> LENGTH: 10
<212> TYPE: PRT
<213> ORGANISM: Artificial
<220> FEATURE:
<223> OTHER INFORMATION: Alternative HIV protease cleavable linker.

<400> SEQUENCE: 42

Ser Ala Thr Ile Met Met Gln Arg Gly Asn
1               5                   10

<210> SEQ ID NO 43
<211> LENGTH: 23
<212> TYPE: PRT
<213> ORGANISM: Artificial
<220> FEATURE:
<223> OTHER INFORMATION: Hydrophilic linker (out-of-frame buforin II).

<400> SEQUENCE: 43

Ile Glu Gly Arg Thr Ser Val Ser Ser Arg Pro Gln Gly Ser Ser Pro
1               5                   10                  15

Leu Thr Glu Val Val Leu Glu
            20
```